(12) United States Patent
Krammer et al.

(10) Patent No.: US 9,445,606 B2
(45) Date of Patent: *Sep. 20, 2016

(54) USE OF 4-HYDROXYDIHYDROCHALCONES AND THEIR SALTS FOR ENHANCING AN IMPRESSION OF SWEETNESS

(75) Inventors: Gerhard Krammer, Holzminden (DE); Jakob Ley, Holzminden (DE); Thomas Riess, Holzminden (DE); Martin Haug, Nördlingen (DE); Susanne Paetz, Höxter (DE); Günter Kindel, Höxter (DE); Ralph Schmidtmann, Holzen (DE)

(73) Assignee: SYMRISE AG, Holzminden (DE)

( * ) Notice: Subject to any disclaimer, the term of this patent is extended or adjusted under 35 U.S.C. 154(b) by 1896 days.

This patent is subject to a terminal disclaimer.

(21) Appl. No.: 12/293,585

(22) PCT Filed: Mar. 21, 2007

(86) PCT No.: PCT/EP2007/052714
§ 371 (c)(1),
(2), (4) Date: Feb. 24, 2010

(87) PCT Pub. No.: WO2007/107596
PCT Pub. Date: Sep. 27, 2007

(65) Prior Publication Data
US 2010/0233102 A1    Sep. 16, 2010

Related U.S. Application Data

(60) Provisional application No. 60/784,444, filed on Mar. 22, 2006.

(30) Foreign Application Priority Data

Jul. 25, 2006  (WO) ............... PCT/EP2006/064633

(51) Int. Cl.
*A61K 47/10* (2006.01)
*A21D 2/02* (2006.01)
(Continued)

(52) U.S. Cl.
CPC . *A21D 2/02* (2013.01); *A21D 2/08* (2013.01); *A21D 2/181* (2013.01); *A21D 2/24* (2013.01);
(Continued)

(58) Field of Classification Search
CPC . A61K 2800/72; A61K 47/10; C11B 9/0061
See application file for complete search history.

(56) References Cited

U.S. PATENT DOCUMENTS 3,087,821 A    4/1963 Horowitz et al.
3,455,702 A *  7/1969 Thomas et al. ............... 426/536
(Continued)

FOREIGN PATENT DOCUMENTS

EP    0774249    *  5/1997
JP    2004018376 A    1/2004
(Continued)

OTHER PUBLICATIONS

Ikan, Raphael. Natural Products: A Laboratory Guide United Kingdom: Academic Press, 1991.*
(Continued)

*Primary Examiner* — Jeffrey S Lundgren
*Assistant Examiner* — Chris Simmons
(74) *Attorney, Agent, or Firm* — Polsinelli PC

(57) ABSTRACT

The invention provides the use of
a 4-hydroxydihydrochalcone of the formula (I)

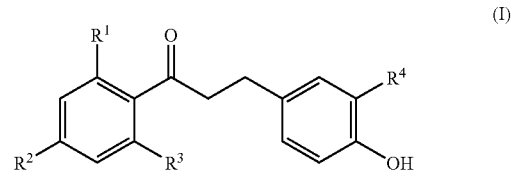

wherein
$R^1$, $R^2$, $R^3$ and $R^4$ each, independently, represent H, OH or O-alkyl, with the proviso that at least one of the groups $R^1$, $R^2$ or $R^3$ represents OH,
a salt of such a 4-hydroxydihydrochalcone of the formula (I),
a mixture containing or consisting of two or more different 4-hydroxydihydrochalcones of the formula (I), wherein $R^1$, $R^2$, $R^3$ and $R^4$ are each defined in the way given above,
a mixture containing or consisting of salts of two or more different 4-hydroxydihydrochalcones of the formula (I), wherein $R^1$, $R^2$, $R^3$ and $R^4$ are each defined in the way given above
or
a mixture containing or consisting of
a 4-hydroxydihydrochalcone of the formula (I) or two or more different 4-hydroxydihydrochalcones of the formula (I), wherein $R^1$, $R^2$, $R^3$ and $R^4$ are each defined in the way given above, and
a salt of a 4-hydroxydihydrochalcone of the formula (I) or two or more salts of different 4-hydroxydihydrochalcones of the formula (I), wherein $R^1$, $R^2$, $R^3$ and $R^4$ are each defined in the way given above,
to enhance the sweet taste of a sweet-tasting substance or the impression of a sweet smell of a flavoring that gives an impression of a sweet smell.

19 Claims, No Drawings

(51) Int. Cl.
| | |
|---|---|
| *A21D 2/08* | (2006.01) |
| *A21D 2/18* | (2006.01) |
| *A21D 2/24* | (2006.01) |
| *A21D 2/26* | (2006.01) |
| *A23C 9/13* | (2006.01) |
| *A23C 9/154* | (2006.01) |
| *A23G 1/32* | (2006.01) |
| *A23G 3/36* | (2006.01) |
| *A23G 4/06* | (2006.01) |
| *A23G 9/32* | (2006.01) |
| *A23L 1/22* | (2006.01) |
| *A23L 1/236* | (2006.01) |
| *A23L 1/307* | (2006.01) |
| *A23L 2/60* | (2006.01) |
| *A61K 8/02* | (2006.01) |
| *A61K 8/35* | (2006.01) |
| *A61K 8/49* | (2006.01) |
| *A61Q 11/00* | (2006.01) |
| *C07C 45/62* | (2006.01) |
| *C07C 45/74* | (2006.01) |
| *C07C 49/84* | (2006.01) |
| *C11B 9/00* | (2006.01) |

(52) U.S. Cl.
CPC ............... *A21D 2/26* (2013.01); *A23C 9/1307* (2013.01); *A23C 9/1544* (2013.01); *A23G 1/32* (2013.01); *A23G 3/36* (2013.01); *A23G 4/06* (2013.01); *A23G 9/32* (2013.01); *A23L 1/22* (2013.01); *A23L 1/22091* (2013.01); *A23L 1/236* (2013.01); *A23L 1/307* (2013.01); *A23L 2/60* (2013.01); *A61K 8/02* (2013.01); *A61K 8/35* (2013.01); *A61K 8/498* (2013.01); *A61Q 11/00* (2013.01); *C07C 45/62* (2013.01); *C07C 45/74* (2013.01); *C07C 49/84* (2013.01); *C11B 9/0061* (2013.01); *A23V 2002/00* (2013.01); *A61K 2800/70* (2013.01)

(56) References Cited

U.S. PATENT DOCUMENTS

| | | |
|---|---|---|
| 3,739,064 A | 6/1973 | Rizzi |
| 3,743,716 A | 7/1973 | Rizzi |
| 3,751,270 A | 8/1973 | Rizzi |
| 3,932,678 A | 1/1976 | Rizzi |
| 4,304,794 A | 12/1981 | Dwivedi et al. |
| 5,895,657 A * | 4/1999 | Fournet et al. ............... 424/401 |
| 2002/0188019 A1 * | 12/2002 | Ley et al. ..................... 514/456 |
| 2003/0017191 A1 * | 1/2003 | Wolf ............................ 424/439 |

FOREIGN PATENT DOCUMENTS

| | | |
|---|---|---|
| JP | 2004043354 A | 2/2004 |
| WO | WO 9822084 * | 5/1998 |

OTHER PUBLICATIONS

Gokmen et al. as (Eur Food Res Technol (2001) 213:194-199).*
Database WPI Week 200419, Derwent Publications Ltd., London, GB; AN 2004-195468, XP002437671 & JP 2004 018376 A (Nikken Kasei KK), Jan. 22, 2004, abstract.
Database WPI Week 200421, Derwent Publications Ltd., London, GB; AN 2004-219112, XP002437672 & JP 2004 043354 A (Nikken Kasei KK), Feb. 12, 2004, abstract.

* cited by examiner

USE OF 4-HYDROXYDIHYDROCHALCONES AND THEIR SALTS FOR ENHANCING AN IMPRESSION OF SWEETNESS

CROSS-REFERENCE TO RELATED APPLICATIONS

This application claims benefit of priority to PCT/EP2006/064633, filed on Jul. 25, 2006, and to U.S. Provisional Application No. 60/784,444, filed on Mar. 22, 2006, which are incorporated herein by reference in their entireties.

The invention primarily provides the use of certain 4-hydroxydihydrochalcones (3-(4-hydroxyphenyl)-1-phenylpropan-1-ones) or their salts for enhancing the sweet taste of sweet-tasting substances or enhancing the impression of a sweet smell of flavourings that give an impression of a sweet smell. The invention thus primarily provides the use of said substances as sweetness enhancers. Further, the invention provides certain preparations that contain an effective concentration of said 4-hydroxydihydrochalcones or their salts and a process for enhancing the sweet taste of a sweet-tasting substance or enhancing the impression of a sweet smell of a flavouring that gives an impression of a sweet smell.

Foodstuffs or items consumed for pleasure that have a high sugar content (in particular sucrose (=saccharose), lactose, glucose or fructose or mixtures of these), are generally greatly preferred by consumers due to their sweetness. On the other hand, it is generally known that a high content of carbohydrates that can be readily metabolised can greatly increase the blood sugar level, lead to the formation of fatty deposits and can ultimately lead to health problems such as overweight, obesity, insulin-resistance, maturity onset diabetes and the consequential illnesses resulting therefrom. In particular, there is the added problem that many of the carbohydrates mentioned above can also impair dental health because they are degraded by certain types of bacteria in the mouth to give, for example, lactic acid and can attack the dental enamel of juvenile or adult teeth (caries).

Therefore, it has long been an objective to reduce the sugar content of foods and/or items consumed for pleasure to the amount that is absolutely necessary, or even less. One appropriate method comprises the use of sweeteners. These are chemically similar substances that have no, or only a very small, calorific value themselves, but at the same time give a strong impression of the sensation of sweetness. These substances are generally non-cariogenic (a review can be found, for example, in the Journal of the American Dietetic Association 2004, 104 (2), 255-275). Although some so-called bulk sweeteners such as sorbitol, mannitol or other sugar alcohols are sometimes excellent sweeteners and can also sometimes replace some of the other nutritional properties of sugars, they lead, in a certain proportion of people, to osmotically related digestive problems when taken too frequently. Although non-nutritive, highly intense sweeteners are extremely suitable for introducing into foodstuffs, due to their low input concentration, they often exhibit taste-related problems due to a time-intensity profile that is not the same as that of sugar (e.g. sucralose, stevioside, cyclamate), a bitter and/or astringent aftertaste (e.g. acesulfame K, saccharin), or a pronounced additional impression of flavouring (e.g. the ammonium salt of glycerrhyzinic acid). Some of the sweeteners are not very thermally stable (e.g. thaumatin, brazzein, monellin) or are not stable in all applications (e.g. aspartame), or else the sweetening effect sometimes lasts for a long time (an intensely sweet aftertaste, e.g. saccharin).

An improvement in the taste-related properties, in particular the aftertaste problems of non-nutritive, highly intense sweeteners, can be achieved by the use of tannic acid, e.g. as described in WO 98/20753, or phenolic acids as described in U.S. Pat. No. 3,924,017. However, such substances are not very stable in applications due to the presence of catechol units.

Another possibility, not involving the use of non-nutritive sweeteners, comprises lowering the sugar content of foods and/or items consumed for pleasure and adding substances that are not perceptible, or are barely perceptible, to the senses, but that, directly or indirectly, enhance the sweetness, as described e.g. in WO 2005/041684. The substances described in WO 2005/041684, however, are expressly of non-natural origin and thus are more difficult to evaluate from a toxicological point of view than substances from natural sources, particularly when the latter occur in foods or items consumed for pleasure or arise from raw materials for producing foods or items consumed for pleasure. EP 1 291 342 describes such substances from natural sources (pyridinium betains); however, these do not act selectively on the sweet taste of the product but also affect other types of taste such as umami or saltiness. In addition, the substances disclosed can be purified only at great cost.

In U.S. Provisional Application 60/702,943 and the documents based thereon (Symrise), the use of hesperetin as a sweetness enhancer for sugar-reduced preparations intended for nutrition or pleasure is recommended. However, a disadvantage of using hesperetin is its low solubility, in particular in clear aqueous applications (such as e.g. clear cola or lemonade) as well as the comparatively weakly expressed sweetness-enhancing effect in acidic foods and items consumed for pleasure.

Therefore it is desirable to find substances that, at low concentrations, effectively enhance the impression of a sweet taste of sweet substances, preferably the impression of a sweet taste of sugar-reduced foods and items consumed for pleasure, in particular sugar-reduced acidic and/or clear aqueous foods and items consumed for pleasure without having a negative effect on any other flavours. It is also desirable to find substances that effectively enhance, in low concentrations, the impression of a sweet smell of flavourings that give an impression of a sweet smell.

The primary object of the present invention was to find substances that (a) are selectively suitable for enhancing the sweet taste of a sweet-tasting substance and/or the impression of a sweet smell of a flavouring that gives an impression of a sweet smell, preferably without having a negative effect on any other flavours, (b) can also be widely used in acidic or clear (aqueous) preparations and preferably (c) occur naturally, preferably in foods or items consumed for pleasure or the corresponding raw materials for preparing these, or are formed during the production of foods or items consumed for pleasure.

In accordance with a first aspect of the present invention, the object mentioned above is achieved by using a 4-hydroxydihydrochalcone of the formula (I)

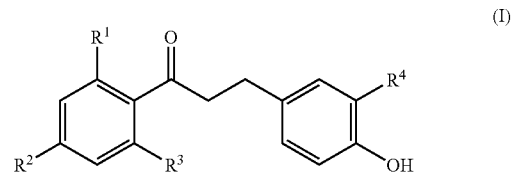

wherein

R¹, R², R³ and R⁴ each, independently, represent H, OH or O-alkyl (preferably with 1 to 4 carbon atoms, i.e. preferably C₁ to C₄ alkoxy), with the proviso that at least one of the groups R¹, R² or R³ represents OH, a salt of such a 4-hydroxydihydrochalcone of the formula (I), a mixture containing or consisting of two or more different 4-hydroxydihydrochalcones of the formula (I), wherein R¹, R², R³ and R⁴ are each defined in the way given above, a mixture containing or consisting of salts of two or more different 4-hydroxy-dihydrochalcones of the formula (I), wherein R¹, R², R³ and R⁴ are each defined in the way given above or a mixture containing or consisting of a 4-hydroxydihydrochalcone of the formula (I) or two or more different 4-hydroxydihydrochalcones of the formula (I), wherein R¹, R², R³ and R⁴ are each defined in the way given above, and a salt of a 4-hydroxydihydrochalcone of the formula (I) or two or more salts of different 4-hydroxydihydrochalcones of the formula (I), wherein R¹, R², R³ and R⁴ are each defined in the way given above, to enhance the sweet taste of a sweet-tasting substance or to enhance the impression of a sweet smell of a flavouring that gives an impression of a sweet smell.

Particularly preferred is a use according to the invention, wherein, in formula (I)

R¹ represents OH

R² and R³, independently, represent H or OH, and

R⁴ represents H or methoxy (OCH₃).

Particularly preferred is the use of a 4-hydroxydihydrochalcone of the formula (I) chosen from the group consisting of 3-(4-hydroxyphenyl)-1-(2-hydroxyphenyl)propan-1-one (2',4-dihydroxydihydrochalcone; compound 1), 3-(4-hydroxyphenyl)-1-(2,4-dihydroxyphenyl)propan-1-one (2',4,4'-trihydroxydihydrochalcone; davidigenin; compound 2), 3-(4-hydroxyphenyl)-1-(2,6-dihydroxyphenyl)propan-1-one (2',4,6'-trihydroxydihydrochalcone; compound 3), 3-(4-hydroxyphenyl)-1-(2,4,6-trihydroxyphenyl)propan-1-one (2',4,4',6'-tetrahydroxydihydrochalcone; phloretin; compound 4), 3-(4-hydroxy-3-methoxyphenyl)-1-(2-hydroxyphenyl)propan-1-one (2',4-dihydroxy-3-methoxydihydrochalcone; compound 5), 3-(4-hydroxy-3-methoxyphenyl)-1-(2,4-dihydroxyphenyl)propan-1-one (2',4,4'-trihydroxy-3-methoxydihydrochalcone; compound 6), 3-(4-hydroxy-3-methoxyphenyl)-1-(2,6-dihydroxyphenyl)propan-1-one (2',4,6'-trihydroxy-3-methoxydihydrochalcone; compound 7), 3-(4-hydroxy-3-methoxyphenyl)-1-(2,4,6-trihydroxyphenyl)propan-1-one (2',4,4',6'-tetrahydroxy-3-methoxydihydrochalcone; compound 8) and 3-(3,4-dihydroxyphenyl)-1-(2,4,6-trihydroxyphenyl)propan-1-one (2',3,4,4',6'-tetrahydroxydihydrochalcone; compound 9), a salt of such a 4-hydroxydihydrochalcone of the formula (I), a mixture containing or consisting of two or more 4-hydroxydihydrochalcones of the formula (I) chosen from said group, a mixture containing or consisting of salts of two or more 4-hydroxydihydrochalcones of the formula (I) chosen from said group or a mixture containing or consisting of a 4-hydroxydihydrochalcone of the formula (I) chosen from said group or two or more 4-hydroxydihydrochalcones of the formula (I) chosen from said group and a salt of a 4-hydroxydihydrochalcone of the formula (I) chosen from said group or two or more salts of different 4-hydroxydihydrochalcones of the formula (I) chosen from said group.

In salts of 4-hydroxydihydrochalcones of the above formula (I) to be used according to the invention, one, several or all of the deprotonatable groups in the 4-hydroxydihydrochalcones of the formula (I) are deprotonated. There is then a corresponding number of gegen-cations present, wherein these are preferably chosen from the group consisting of: a cation with a single positive charge from group 1a or 1b, ammonium ions, trialkylammonium ions, cations with two positive charges from group 2a or 2b and also cations with three positive charges from group 3a or 3b, and mixtures of these.

Particularly preferred cations are Na⁺, K⁺, NH₄⁺, Ca²⁺, Mg²⁺, Al³⁺ and Zn²⁺.

From among the particularly preferred compounds, 3-(4-hydroxy-3-methoxyphenyl)-1-(2,4,6-trihydroxyphenyl)propan-1-one (2',4,4',6'-tetrahydroxy-3-methoxydihydrochalcone; compound 8) is novel.

For clarification, the preferred compounds are specified once again in the figure given below (by way of example, the general numbering scheme for dihydrochalcones is given on compound 1):

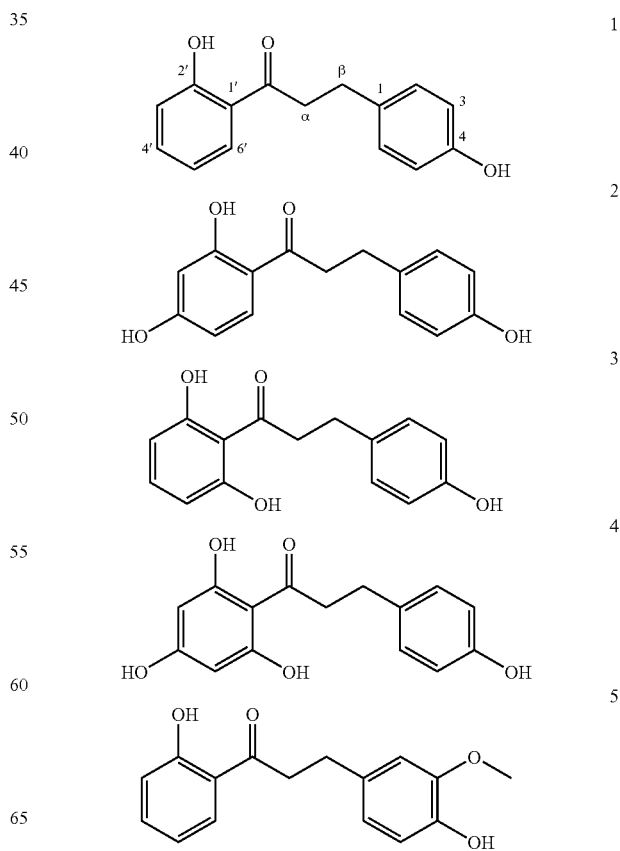

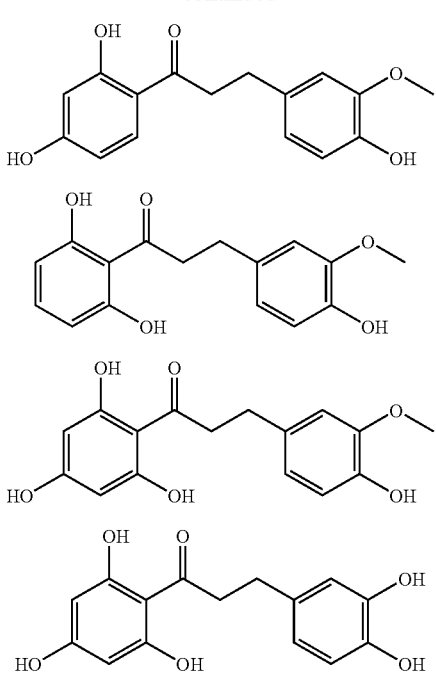

The previously mentioned substances and substance mixtures used according to the invention are preferably used to enhance the sweet taste of a sweet-tasting substance or the impression of a sweet smell of a flavouring that gives an impression of a sweet smell in a preparation that is used for nutrition, oral hygiene or pleasure.

The invention also provides, in addition to the use of certain substances or substance mixtures as explained hitherto, in accordance with another aspect of the invention, corresponding preparations in which the said substances or substance mixtures are used in the manner according to the invention.

A preparation according to the invention is thus preferably selected from the group consisting of preparations, semi-finished products, odour-providing, flavour-providing or taste-providing compositions or spice mixtures that are used for nutrition, oral hygiene or pleasure. A preparation according to the invention contains the following components:

(a)
a 4-hydroxydihydrochalcone of the formula (I)

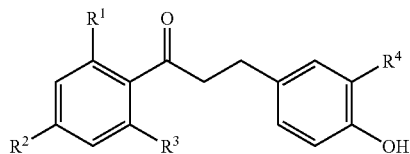

wherein $R^1$, $R^2$, $R^3$ and $R^4$ each, independently, represent H, OH or O-alkyl (alkoxy; preferably with 1 to 4 carbon atoms, see above), with the proviso that at least one of the groups $R^1$, $R^2$ or $R^3$ represents OH, a salt of such a 4-hydroxydihydrochalcone of the formula (I), a mixture containing or consisting of two or more different 4-hydroxydihydrochalcones of the formula (I), wherein $R^1$, $R^2$, $R^3$ and $R^4$ are each defined in the way given above, a mixture containing or consisting of salts of two or more different 4-hydroxy dihydrochalcones of the formula (I), wherein $R^1$, $R^2$, $R^3$ and $R^4$ are each defined in the way given above or a mixture containing or consisting of a 4-hydroxydihydrochalcone of the formula (I) or two or more different 4-hydroxydihydrochalcones of the formula (I), wherein $R^1$, $R^2$, $R^3$ and $R^4$ are each defined in the way given above, and a salt of a 4-hydroxydihydrochalcone of the formula (I) or two or more salts of different 4-hydroxydihydrochalcones of the formula (I), wherein $R^1$, $R^2$, $R^3$ and $R^4$ are each defined in the way given above, as well as (b) one or more other sweet-tasting substances and/or (c) one or more flavourings that give an impression of a sweet smell, wherein the total amount of component (a) in the preparation is sufficient to enhance the sensation of the impression of a sweet taste of the sweet-tasting substance(s) (b) or the impression of a sweet smell of the flavouring(s) (c) that give an impression of a sweet smell, preferably in a overproportional manner (i.e. over and above the effect provided by the actual sweetness).

With regard to the preferred definitions of groups $R^1$, $R^2$, $R^3$ and $R^4$ in formula (I) the same applies here as was stated above in connection with the use according to the invention.

Here again, in the preparations according to the invention, the presence of a 4-hydroxydihydrochalcone of the formula (I) selected from the group consisting of compounds 1 to 9, a corresponding salt or a corresponding mixture (as given above in detail) is preferred.

It should be pointed out at this point that each of the specifications with regard to preferred variants of a use according to the invention, a preparation according to the invention or a process according to the invention, all apply equally to the other aspects of the invention.

A preferred preparation according to the invention contains, as component (b), one or more sugars, wherein the total amount of (i) 4-hydroxydihydrochalcones of the formula (I) and (ii) their salts (component (a)) in the preparation is sufficient to convey the same or an enhanced impression of sweetness as a preparation or semi-finished product with an otherwise identical composition that contains neither (i) 4-hydroxydihydrochalcones of the formula (I) nor (ii) their salts, but at least 1.05 times the amount (preferably at least 1.2 times the amount, more preferably at least 1.4 times the amount) of sugar. The sugars in this case are preferably chosen from the group consisting of: sucrose, lactose, glucose, fructose and mixtures of these.

Many of the 4-hydroxydihydrochalcones of the formula (I), that are to be used according to the invention and are present in preparations according to the invention are known per se. Thus, 2',4,6'-trihydroxydihydrochalcone (compound 3) and 2',4,6'-trihydroxy-3-methoxydihydrochalcone (compound 7) were described in the Chemical & Pharmaceutical Bulletin 1977, 25 (6), 1484-1486.

The 4-hydroxydihydrochalcones (or their salts and mixtures) to be used according to the invention can be of natural origin (e.g. from plant partial extracts, by converting natural precursor molecules such as phloridzin (a glycoside of phloretin) or naringin or naringenin using enzymatic or other processes). However, the substances or substance mixtures to be used according to the invention may also be purely synthetic.

Phloretin (compound 4) occurs as the free compound in particular in certain rosacea plants, in particular in apple trees and processed apple tree products, e.g. in apple juice or other apple fruit products, apple leaf extracts, apple root extracts etc. (Journal of Chromatography, A 2001, 910 (2), 265-273). 3-hydroxyphloretin (compound 9) has also been found in apple products (J. Agric. Food Chem. 2003, 51 (21), 6347-6353).

4-hydroxydihydrochalcones of the formula (I) to be used according to the invention (and likewise their salts) can be synthesised using methods known per se from the literature, e.g. by reducing the corresponding chalcones, wherein the chalcones can be produced by Knoevenagel condensation of a corresponding acetophenone with an aldehyde or by ring-opening of the corresponding flavanones (J. Agric. Food Chem. 2003, 51, 3309-3312). Alternatively, dihydrochalcones can also be obtained directly by acylation of mono-, di- or triphenols using a corresponding dihydrocinnamic acid, e.g. 4-hydroxydihydrocinnamic acid or dihydroferulic acid and Lewis acids, e.g. boron trifluoride complexes (Tetrahedron 2006, 62 (5), 841-846). If the 4-hydroxydihydrochalcones of the formula (I) to be used according to the invention, or their salts, are naturally occurring, then they can be obtained from the corresponding biogenic precursor glycosides using chemical- or enzyme-catalysed hydrolysis; e.g. phloretin from phloridzin. In so far as phloretin occurs as the free compound in certain natural products, e.g. apple products, the precursor glycoside phloridzin is also always present alongside it. Normally, the phloretin content is clearly below 10 ppm, e.g. up to a maximum of 1.1 ppm in stewed apple: J. Chem. Ecol. 2000, 26(10), 2275-2290, or 0.3-7 ppm in apple wine: Food Chemistry 2006, 97(3), 438-446. The proportion of phloridzin is then regularly the greater by one or more orders of magnitude. The use of phloridzin in preparations according to the invention, however, is not desirable because phloridzin has a very bitter taste (B. A. Bohm, Introduction to Flavonoids, Harwood Academic Publishers, 1998, p. 378 et seq.). Moreover, the natural total polyphenol content in phloretin/phloridzin-rich apple products is altogether high (Deutsche Lebensmittel-Rundschau 2006, 102(9), 426-435 and J. Sci. Food Agric. 2005, 85(10), 1687-1694); the associated catechins (e.g. (–)-epicatechin, procyanidins), phenolic acid derivatives (e.g. protocatechuic acid, chlorogenic acid) and flavones (e.g. rutin), however, are known to cause a bitter and/or astringent taste, which may have a negative influence on the sweetness of the product.

All in all, the use of glycosides of 4-hydroxydihydrochalcones of the formula (I) (or their salts) is not preferred, according to the invention.

In a preferred preparation according to the invention, the ratio of the total amount of (i) 4-hydroxydihydrochalcones of the formula (I) and (ii) their salts contained therein to the total amount of glycosides of the (i) 4-hydroxydihydrochalcones of the formula (I) and (ii) their salts used is greater than 1:3, preferably greater than 1:1, particularly preferably greater than 10:1.

Preparations according to the invention that contain phloretin (compound 4) are very particularly preferred. Such preparations according to the invention preferably have only a small proportion of, or no, glycosides of phloretin. The ratio of the amount of phloretin to the amount of phloretin glycosides is preferably greater than 1:3, more preferably greater than 1:1, particularly preferably greater than 10:1. A preferred phloretin-containing preparation according to the invention contains (a) no phloridzin
or
(b) phloridzin, wherein the ratio of the amount of phloretin to the amount of phloridzin is greater than 1:3, preferably greater than 1:1, particularly preferably greater than 10:1.

Thus (sugar-reduced) preparations according to the invention that contain one or more sugars as the sweet-tasting substance or sweet-tasting substances are preferred, wherein the amount of (i) 4-hydroxydihydrochalcones of the formula (I) and/or (ii) their salts added is sufficient to convey the same or an enhanced impression of sweetness as a preparation with an otherwise identical composition that contains neither 4-hydroxydihydrochalcones nor their salts but at least 1.05 times, preferably at least 1.2 times, particularly preferably at least 1.4 times, the amount of sugar. The sugars are then preferably chosen from the group consisting of: sucrose, lactose, glucose, fructose and mixtures of these.

A preferred preparation according to the invention (as described above, in particular in a preferred variant) contains (b) one or more further sweet-tasting substances, wherein the further sweet-tasting substance(s) are chosen from the group consisting of:

(i) one or more carbohydrates (sugars) chosen from the group consisting of sucrose, trehalose, lactose, maltose, melizitose, melibiose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, maltodextrin and plant preparations containing one or more of the carbohydrates mentioned (preferably in a proportion of at least 5 wt. %, more preferably at least 15 wt. %), wherein these carbohydrates may also be present as a natural or artificially produced mixture (e.g. as honey, invert sugar syrup, highly enriched fructose syrups from maize starch [High Fructose Corn Syrup])

(ii) one or more sugar alcohols chosen from the group consisting of glycerine, erythritol, threitol, arabitol, ribitol, xylitol, sorbitol, mannitol, maltitol, isomaltitol, dulcitol and lactitol, (iii) one or more proteins and/or amino acids from the group consisting of miraculin, monellin, thaumatin, curculin, brazzein, glycine, D-leucine, D-threonine, D-asparagine, D-phenylalanine, D-tryptophan, L-proline or extracts or fractions obtained from natural sources, the extracts or fractions containing these amino acids and/or proteins, (iv) one or more sweet substances from the group consisting of magap, sodium cyclamate, acesulfame K, neohesperidin dihydrochalcone, sodium salt of saccharin, aspartame, superaspartame, neotam, alitam, sucralose, stevioside, rebaudioside, lugduname, carrelame, sucrononate, sucrooctate, monatin and phyllodulcin, wherein in case of the naturally occurring sweet substances also extracts or enriched fractions of these extracts may be used, e.g. stevia extracts, citrus extracts, buddah tea extracts, and mixtures of these
and/or (c) one or more flavourings that give an impression of a sweet smell, wherein the further flavouring(s) that give an impression of a sweet smell are chosen from the group consisting of:

vanillin, ethylvanillin, ethylvanillin isobutyrate (=3-ethoxy-4-isobutyryloxybenzaldehyde), Furaneol® (2,5-dimethyl-4-hydroxy-3(2H)-furanone) and derivatives thereof (e.g. homofuraneol, 2-ethyl-4-hydroxy-5-methyl-3(2H)-furanone), homofuronol (2-ethyl-5-methyl-4-hydroxy-3 (2H)-furanone and 5-ethyl-2-methyl-4-hydroxy-3(2H)-furanone), maltol and derivatives thereof (e.g. ethyl maltol), coumarin and derivatives thereof, gamma-lactones (e.g. gamma-undecalactone, gamma-nonalactone), delta-lactones (e.g. 4-methyl-deltalactone, massoilactone, deltadecalactone, tuberolactone), methyl sorbate, divanillin, 4-hydroxy-2(or 5)-ethyl-5(or 2)-methyl-3(2H)furanone, 2-hydroxy-3-methyl-2-cyclopentenone, 3-hydroxy-4,5-dimethyl-2(5H)-furanone, fruit esters and fruit lactones (e.g. n-butyl acetate, isoamyl acetate, ethyl propionate, ethyl butyrate, n-butyl butyrate, isoamyl butyrate, ethyl 3-methylbutyrate, ethyl n-hexanoate, allyl n-hexanoate, n-butyl n-hexanoate, ethyl n-octanoate, ethyl-3-methyl-3-phenyl glycidate, ethyl 2-trans-4-cis-decadienoate), 4-(p-hydroxyphenyl)-2-butanone, 1,1-dimethoxy-2,2,5-trimethyl-4-hexane, 2,6-dimethyl-5-hepten-1-al and phenylacetaldehyde.

The sweet tasting substances used are preferably from the group consisting of (a) sucrose, lactose, D-glucose, D-tagatose and D-fructose, wherein these carbohydrates may also be present as a natural or artificially produced mixture (e.g. as honey, invert sugar, highly enriched fructose syrups from maize starch [High Fructose Corn Syrup])

(b) erythritol, threitol, arabitol, ribitol, xylitol, sorbitol, mannitol, maltitol, isomaltitol, dulcitol and lactitol, (c) thaumatin, glycine, D-phenylalanine, D-tryptophan, (d) sweet substances from the group sodium cyclamate, acesulfame K, neohesperidin dihydrochalcone, sodium salt of saccharin, aspartame, superaspartame, neotam, alitam, sucralose, stevioside, wherein the amount of added (i) 4-hydroxydihydrochalcone and (ii) its salt in the preparation is sufficient to enhance the impression of a sweet taste of the sweet-tasting substance(s); the total amount of 4-hydroxydihydrochalcones of the formula (I) or their salts is then preferably in the range 0.1 to 150 ppm, more preferably in the range 1 to 50 ppm, particularly preferably in the range 10 to 50 ppm, with respect to the total weight of the preparation.

A synergistic increase in the impression of a sweet taste may (as mentioned above) be produced in particular with these combinations.

Preferred sweet-tasting substances have been cited above. In general, however, sweet-tasting substances (including natural sources of these substances) may be, for example: sweet-tasting carbohydrates or sugars (e.g. sucrose (synonym for saccharose), trehalose, lactose, maltose, melizitose, melibiose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, maltodextrin) or plant preparations containing mainly these carbohydrates (e.g. from sugar beet (*Beta vulgaris* ssp., sugar fractions, sugar syrups, molasses), from sugar cane (*Saccharum officinarum* ssp., e.g. molasses, sugar syrups), from sugar maple (*Acer* ssp.), from agave (concentrated agave juice), artificial/enzymatic hydrolysates of starch or sucrose (e.g. invert sugar syrup, highly enriched fructose syrup from maize starch), fruit concentrates (e.g. from pears, pear foliage)), sugar alcohols (e.g. glycerine, erythritol, threitol, arabitol, ribitol, xylitol, sorbitol, mannitol, maltitol, isomaltitol, dulcitol, lactitol), proteins (e.g. miraculin, monellin, thaumatin, curculin, brazzein), sweeteners (magap, sodium cyclamate, acesulfame K, neohesperidin dihydrochalcone, sodium salt of saccharin, aspartame, superaspartame, neotam, alitam, sucralose, stevioside, rebaudioside, lugduname, carrelame, sucrononates, sucrooctates, monatin, phyllodulcin), certain sweet-tasting amino acids (glycine, D-leucine, D-threonine, D-asparagine, D-phenylalanine, D-tryptophan, L-proline), other sweet-tasting low molecular weight substances (e.g. hernandulcin, isocoumarins such as phyllodulcin or hydrangenol, dihydrochalcone glycosides such as neophesperidine dihydrochalcones, glycyrrhizins, ammonium salt of glycyrrhetinic acid or other glycyrrhetinic acid derivatives), extracts of liquorice (*Glycyrrhizza glabra* ssp.), extracts of Lippia dulcis, extracts or individual substances from *Momordica* ssp. (in particular *Momordica grosvenori* [Luo Han Guo] and the mogrosides obtained therefrom), from *Hydrangea dulcis* or from *Stevia* ssp. (z.B. *Stevia rebaudiana*).

The previously mentioned preferred flavourings are flavourings that give an impression of a sweet smell, i.e. flavourings that although they are not sweet in the strict sense can suggest a sweet taste in the wider sense (in particular including the perception of a smell).

The invention relates to the surprising finding that the 4-hydroxydihydrochalcones of the formula (I) (or their salts and mixtures, as cited above) to be used according to the invention, even in very small concentrations (less than 0.025 wt. %, compare the concentration ranges referred to below) increase the impression of a sweet taste of sweet-tasting substances (as cited above), but in particular of sugars such as sucrose, lactose, glucose, D-tagatose and fructose as well as sugar alcohols such as e.g. glycerine, erythritol, threitol, arabitol, ribitol, xylitol, sorbitol, mannitol, dulcitol, lactitol, to an overproportional extent (i.e. synergistically) and it is thus possible to lower the sugar content in appropriate foods and items consumed for pleasure without at the same time reducing the impression of a sweet taste. In low concentrations (compare the preferred concentrations for use given below) the 4-hydroxydihydrochalcones of the formula (I) or their salts to be used according to the invention exhibit only a very slight taste of their own. The 4-hydroxydihydrochalcones of the formula (I) and their salts are also used in particular in acidic foods and items consumed for pleasure, in particular those with a pH in the range 1 to 6, preferably in the range 2 to 4. The 4-hydroxydihydrochalcones or their salts to be used according to the invention dissolve in the preferred concentrations in aqueous systems to give a clear solution, which means that they are especially suitable for use in clear, sweet-acidic soft drinks. Preferred concentrations in this case are less than 0.01 wt. % (100 ppm), preferably less than 0.006 wt. % (60 ppm), in particular less than 0.004 wt. % (40 ppm), more preferably in the range 1 to 30 ppm and most preferably in the range 10 to 30 ppm.

The sweet taste of a sweet tasting substance or the impression of a sweet smell of a flavouring that gives an impression of a sweet smell is preferably enhanced in a preparation that is intended for nutrition, oral hygiene or pleasure.

A preferred preparation is a preparation intended for nutrition, oral hygiene or pleasure (in particular in one of the variants previously cited as particularly preferred) containing a total amount of less than 0.025 wt. % (250 ppm), preferably less than 0.02 wt. % (200 ppm), of (i) 4-hydroxydihydrochalcones of the formula (I) and (ii) their salts, with respect to the total weight of preparation.

Even in these low concentrations, the 4-hydroxydihydrochalcones used, or their salts or corresponding mixtures, significantly enhance the sensation of sweetness of sweet-tasting substances or flavourings that give an impression of a sweet smell.

Preparations intended for nutrition, oral hygiene or pleasure (as described previously, in particular in the variants cited as particularly preferred) that are particularly preferred are those containing a total amount of (i) 4-hydroxydihydrochalcones of the formula (I) and (ii) their salts in the range 0.1 to 150 ppm, preferably in the range 1 to 50 ppm, particularly preferably in the range 10 to 50 ppm, with respect to the total weight of the preparation.

By using, according to the invention, (i) 4-hydroxydihydrochalcones of the formula (I) and (ii) their salts, it is possible in particular to lower the proportion of sweet-tasting substances, in particular however of sugars such as sucrose, lactose, fructose and/or glucose or mixtures thereof, by 5 to 60% (with respect to the sweet-tasting substance(s)), as compared with a preparation with no (i) 4-hydroxydihydrochalcones to be used according to the invention, or (ii) their salts, without thereby reducing the impression of a sweet taste.

Preferred preparations according to the invention, that may be sugar-free, sugar-reduced or sugar-containing, and are used in particular for nutrition, oral hygiene or pleasure, are chosen from the group consisting of:

(A) confectionery, e.g. white, milk or dark chocolate, filled chocolates (filled, for example, flavoured fondant materials, like after-eights), chocolate bars, other bar products, chews, fruit gums, hard and soft caramels, chewing gum, sugar drops, lollipops), capsules (preferably seamless capsules for direct consumption, preferably with a coating based on gelatine and/or alginate), chewing gum (e.g. in the form of strips, compressed tablets, pellets, cushions, spheres, hollow spheres), (B) alcoholic or non-alcoholic drinks or instant drinks, in particular coffee, tea, wine, wine-containing drinks, beer, beer-containing drinks, liqueurs, schnapps, brandy, fruit-containing lemonades, isotonic drinks, soft drinks, crushed fruit drinks, fruit and vegetable juices with the exception of non-modified apple products, fruit or vegetable juice preparations, instant cocoa drinks, instant tea drinks, instant coffee drinks, (C) cereal products and/or nut products, in particular breakfast cereals, cornflakes, oat flakes, bulk muesli, muesli bars, student food, sweet popcorn, nut bars, fruit-and-nut bars, pre-cooked ready-to-eat rice products, (D) milk products, in particular milk drinks, milk-based ice-cream, diet ice-cream, yoghurts, blancmanges, kefir, fresh cheese, soft cheese, hard cheese, dried milk powder, whey, butter, buttermilk, partly or fully hydrolysed milk-protein-containing products, (E) fruit and/or vegetable preparations, in particular jams, diabetic marmalades, fruit ice-creams, fruit sauces, fruit fillings with the exception of natural apple products, ketchup, sauces, dried vegetables, deep-frozen vegetables, pre-cooked vegetables, vegetables stored in vinegar, preserved vegetables, (F) products based on fats and oils or the emulsions themselves, in particular mayonnaises, remoulades, dressings, herb preparations, (G) an oral care product (oral hygiene product), in particular in the form of a toothpaste, tooth cream, tooth gel, tooth powder, tooth polishing liquid, tooth polishing foam, mouthwash, mouthwash concentrate, tooth cream and mouthwash as a 2-in-1 product, lozenges, mouthspray, tooth floss, chewing gum or dental care chewing gum.

The amount of (i) 4-hydroxydihydrochalcones of the formula (I) and (ii) their salts in a preparation according to the invention is preferably sufficient to enhance the impression of a sweet taste or impression of a sweet smell significantly, by at least 10%, with respect to a comparison formula with an otherwise identical composition that contains neither 4-hydroxydihydrochalcones of the formula (I) nor their salts.

It has already been pointed out that free phloretin and 3-hydroxyphloretin, i.e. 4-hydroxydihydrochalcones of the formula (I) that, differently from e.g. phloridzin, contain no sugar groupings, occur in natural products, in particular in apple products. Preparations according to the invention are not these types of natural products. In fact in natural products, the amount of (i) 4-hydroxydihydrochalcones of the formula (I) and (ii) their salts (e.g. the amount of phloretin and its salts) is usually not sufficient to significantly enhance the impression of a sweet taste of a sweet-tasting substance present in the naturally occurring product or the impression of a sweet smell of a flavouring that gives an impression of a sweet smell present in the naturally occurring product. Thus it is not possible to lower the proportion of sweet-tasting substances in the natural product, in particular, however, the proportion of sucrose, lactose, fructose, glucose, or mixtures of these, to a significant extent, e.g. by 5 to 60% wt. % (with respect to the total amount of sweet-tasting substances) without thereby decreasing the impression of a sweet taste (compare also the above statements with regard to the associated polyphenols).

The proportion of the sweet-tasting substances mentioned in a natural product can, however, be lowered without decreasing the impression of a sweet taste if at the same time the proportion of phloretin or another 4-hydroxydihydrochalcone of the formula (I) or a corresponding salt or a corresponding mixture (as described above, preferably in one of the preferred variants) is increased. In particular, the use of an elevated amount of a 4-hydroxydihydrochalcone of the formula (I) (or a corresponding salt or a corresponding mixture) and retention of the same impression of a sweet taste is possible with a reduction in the proportion of sweet-tasting substance(s) by more than 5 wt. %, preferably more than 15 wt. %, particularly preferably more than 40 wt. % (with respect to the amount of sweet-tasting substances in the natural product).

It has already been pointed out that one or more of the compounds 1 to 9 mentioned above (preferably phloretin, compound 4) are preferably used in a corresponding preparation according to the invention and that the ratio of the total amount of (i) 4-hydroxydihydrochalcones of the formula (I) and (ii) its salts contained therein to the total amount of glycosides of the (i) 4-hydroxydihydrochalcones of the formula (I) and (ii) their salts used is preferably greater than 1:3, more preferably greater than 1:1 in a preparation according to the invention.

Preparations that contain at least one sweet-tasting substance, preferably a sugar such as sucrose, lactose, glucose and/or fructose, are particularly relevant, wherein the amount of sweet-tasting substance is not sufficient to convey a satisfyingly sweet taste in a comparison preparation that contains no 4-hydroxydihydrochalcones of the formula (I) (or a corresponding salt or corresponding mixture), but has an otherwise identical composition, wherein the amount of 4-hydroxydihydrochalcones of the formula (I) (or a corresponding salt or a corresponding mixture, preferably in one of the variants cited above as preferred) present in the preparation is sufficient to enhance the impression of sweetness of the sweet-tasting substance, preferably to the extent that a satisfyingly sweet taste is conveyed overall. It has already been specified above that the total amount of (i) 4-hydroxydihydrochalcones of the formula (I) and (ii) their salts (component (a)) in the preparation is preferably sufficient to convey the same or an enhanced impression of a sweet taste when compared with a preparation with an otherwise identical composition that contains neither (i) 4-hydroxydihydrochalcones of the formula (I) nor (ii) their salts but contains at least 1.05 times the amount (preferably at least 1.2 times the amount, particularly preferably at least 1.4 times the amount) of sugar.

Preferred preparations according to the invention are preparations intended for nutrition, oral hygiene or pleasure, the compositions of which comply with the aforesaid.

Preparations according to the invention and intended for nutrition, oral hygiene or pleasure are usually products that are specified for introduction into a person's mouth, remain there for a certain length of time and are then either eaten (e.g. consumable foodstuffs) or removed from the mouth again (e.g. chewing gum or toothpaste). It is understood that the use of 4-hydroxydihydrochalcones of the formula (I) or their salts or corresponding mixtures is intended for any type of product of this kind. These products therefore include all substances or products that are intended to be placed, in a processed, partly processed or non-processed state, in a person's mouth. This also includes substances that are added to foodstuffs during the production, processing or treatment thereof and that are intended to be placed in a person's mouth.

It is understood that the 4-hydroxydihydrochalcones of the formula (I) or their salts or corresponding mixtures to be used according to the invention can be used in particular in foodstuffs. In the context of the present text, "foodstuffs" are understood to be in particular substances that are intended to be swallowed by people in the unaltered, treated or processed state and then to be digested. Coverings, coatings or other outer portions are also understood to be foodstuffs in so far as they are intended also to be swallowed or the swallowing of which can be foreseen. Certain products that are generally removed from the mouth again (e.g. chewing gums) are also understood to be foodstuffs in the context of the present text because it cannot be excluded that at least some part of them might be swallowed.

The 4-hydroxydihydrochalcones of the formula (I) or their salts or their corresponding mixtures to be used according to the invention are used in particular in ready-to-eat foodstuffs. A ready-to-eat foodstuff is understood to be a foodstuff that already contains all the substances that are critical to the taste. The expression "ready-to-eat foodstuffs" also includes corresponding drinks as well as solid or semi-solid ready-to-eat foodstuffs. Examples that may be mentioned include deep-frozen products that have to be thawed and heated to the eating temperature before being eaten. Products such as yoghurts or ice-creams, but also chewing gums and hard toffees are also included among ready-to-eat foodstuffs.

The 4-hydroxydihydrochalcones of the formula (I) or their salts to be used according to the invention may also be used in semi-finished foodstuffs. The expression semi-finished foodstuffs refers here to foodstuffs that are intended to be eaten only in a further-processed state, after adding flavourings or taste-providing substances that are critical to (or one of the critical factors for) the final sensation.

A preparation intended for oral hygiene purposes (oral care product or oral hygiene product or oral hygiene preparation) in the context of the invention is understood to be a preparation for the cleaning and care of the mouth and throat as well as for freshening the breath. Care of the teeth and gums is expressly included here. The forms of presentation of common oral hygiene formulations are creams, gels, pastes, foams, emulsions, suspensions, aerosols, sprays and also capsules, granules, pastilles, tablets, lozenges or chewing gums, without this list being understood to be restrictive for the purposes of this invention.

Further conventional active ingredients, basic materials, auxiliary substances and additives for the preparations according to the invention and intended for nutrition, oral hygiene or pleasure may be present in amounts of 5 to 99.999999 wt. %, preferably 10 to 80 wt. %, with respect to the total weight of the preparation. Furthermore, the preparations may contain water in an amount up to 99.999999 wt. %, preferably 5 to 80 wt. %, with respect to the total weight of the preparation.

The present invention provides in particular a preparation that is intended for nutrition, oral hygiene or pleasure, that contains a component (a), that contains phloretin or consists of phloretin, a component (b) (i.e. one or more sweet-tasting substances) containing or consisting of one or more sugars, as well as, optionally component (c) (i.e. one or more flavourings that give the impression of a sweet smell)

wherein the total amount of component (a) in the preparation (i.e. the total amount of 4-hydroxydihydrochalcones of the formula (I) as described above, their salts or corresponding mixtures)

is sufficient to convey the same or an enhanced impression of a sweet taste when compared with a preparation with an otherwise identical composition that contains neither (i) 4-hydroxydihydrochalcones of the formula (I) nor (ii) their salts but contains at least 1.05 times the amount of sugar and/or is present in the range 0.1 to 150 ppm, and wherein the preparation either (A) contains no phloridzin or (B) contains phloridzin, wherein the ratio of the amount of phloretin to the amount of phloridzin is greater than 1:3, preferably greater than 1:1, particularly preferably greater than 10:1.

Further preferred preparations according to the invention are semi-finished products, odour-providing, flavour-providing or taste-providing compositions or mixtures of spices.

The expression semi-finished products includes in particular semi-finished foodstuffs, i.e. foodstuffs that are intended to be eaten only in a further-processed state, after adding flavourings or taste-providing substances that are critical to (or one of the critical factors for) the final sensation.

Semi-finished products according to the invention may also be presented in a spray-dried form. Preparations according to the invention may also be presented as food supplements in the form of capsules, tablets (uncoated and coated tablets, e.g. gastric acid-resistant coatings), dragees, granules, pellets, mixtures of solids, dispersions in a liquid phase, as emulsions, as powders, as solutions or as other swallowable or chewable preparations.

Preparations according to the invention that are presented as semi-finished products may be used in particular to enhance the impression of a sweet taste of the final preparations that are produced using the semi-finished preparation and are used for the purposes of nutrition, oral hygiene or pleasure.

Spray-dried solid preparations according to the invention in the form of semi-finished products are particularly well suited for producing preparations according to the invention that can be used in particular for nutrition, oral hygiene or pleasure. In the spray-dried semi-finished products, in fact, the solubility of the 4-hydroxydihydrochalcones of the formula (I) or their salts to be used according to the invention is substantially improved by the supporting materials and/or auxiliary substances, in particular by maltodextrin, starches, natural or artificial polysaccharides and/or plant gums such as modified starches or gum arabica. Spray-dried solid semi-finished products according to the invention preferably contain 50 to 95 wt. % of supporting substances, in particular maltodextrin and/or starch, 5 to 40 wt. % of auxiliary substances, preferably natural or artificial polysaccharides and/or plant gums such as modified starches or gum arabica and 1 to 45 wt % of 4-hydroxydihydrochalcones of the formula (I) or their salts to be used according to the invention, with respect to the total weight of the spray-dried solid preparation.

Preparations according to the invention that are chosen from the group consisting of semi-finished products, odour-providing, flavour-providing or taste-providing compositions or mixtures of spices, contain a total amount of (i) 4-hydroxydihydrochalcones of the formula (I) or (ii) their salts in the range 0.0001 wt.-% to 95 wt. %, preferably 0.001 wt. % to 80 wt. %, particularly preferably 0.001 wt. % to 50 wt. %, with respect to the total weight of the preparation.

Preparations according to the invention may also contain a flavour composition in order to round out and refine the taste and/or smell of the preparation. Suitable flavour compositions contain e.g. flavour-providing, odour-providing and taste-providing substances that are synthetic, natural or identical to natural products as well as suitable auxiliary substances and support materials. Particularly preferred preparations according to the invention contain one or more flavourings that give an impression of the smell of "sweetness" (see above).

Semi-finished products according to the invention usually contain other taste-providing and/or flavour-providing substances, in particular flavourings that give an impression of a sweet smell (for comparison, see above), as well as suitable solvents (e.g. ethanol, glycerine, 1,2-propylene glycol, alkyl esters of lactic acid, ethyl esters of organic fruit acids such as diethyl malonate, diethyl tartrate, diethyl malate, triethyl citrate, diethyl succinate, diethyl fumarate, diethyl maleate) and other auxiliary agents (e.g. colorants, pigments, antioxidants, preservatives, emulsifiers, viscosity-changing substances).

Spray-dried solid semi-finished products according to the invention preferably contain 1 to 50 wt. % of the 4-hydroxydihydrochalcones or their salts or corresponding mixtures being used according to the invention, with respect to the total weight of the preparation, 0 to 10 wt. %, preferably 1 to 10 wt. % of other flavourings, 50 to 99 wt. % of support materials and 0 to 50 wt. % preferably 1 to 50 wt. % of other auxiliary substances and/or stabilisers, each with respect to the total weight of the preparation.

Advantageous support materials in spray-dried solid preparations according to the invention are carbohydrates and/or carbohydrate polymers (polysaccharides). Preferred support materials in the flavour particles to be used according to the invention that may be mentioned are, for example, hydrocolloids such as starches, degraded starches, chemically or physically modified starches, modified celluloses, gum arabica, gum ghatti, gum tragacanth, karaya, carrageenan, guar seed flour, carob seed flour, alginates, pectin, inulin or xanthan gum, dextrins and maltodextrins.

The degree of degradation of starch is measured using the characteristic the "dextrose equivalent" (DE) and this can assume the limiting values 0 for long-chain glucose polymer starches and 100 for pure glucose.

Particularly preferred support materials for the spray-dried solid preparations according to the invention are maltodextrins, wherein maltodextrins with DE values in the range 10 to 30 are again of advantage here.

It has already been mentioned that spray-dried solid semi-finished products are particularly good for producing preparations according to the invention that are intended to be used for nutrition, oral hygiene or pleasure.

As already mentioned, (i) 4-hydroxydihydrochalcones of the formula (I) or their salts are not always very soluble in conventional (suitable for consumption) solvents. Therefore, in the context of the present invention, there is the additional object of improving the solubility of the (i) 4-hydroxydihydrochalcones of the formula (I) or their salts and corresponding mixtures to be used according to the invention. In particular in odour-providing, flavour-providing or taste-providing compositions but also in general in preparations being used for nutrition, oral hygiene or pleasure. According to the invention, this object is achieved by the use of an additional component (d) in a preparation according to the invention, wherein component (d) includes esters and/or solvents.

A preferred preparation according to the invention contains, as additional component (d)

one or more esters chosen from the group consisting of $C_1$-$C_6$-esters of lactic acid, di-$C_1$-$C_4$-esters of tartaric acid, di-$C_1$-$C_4$-esters of succinic acid, di-$C_1$-$C_4$-esters of malonic acid, di-$C_1$-$C_4$-esters of malic acid, di-$C_1$-$C_4$-esters of citric acid and tri-$C_1$-$C_4$-esters of citric acid, and/or one or more solvents chosen from the group consisting of 1,2-propylene glycol, dimethylsulfoxide, ethanol and ethanol/water mixtures.

In addition to additional component (d), one or more further flavourings are preferably present, in particular flavourings that give an impression of a sweet smell and thus are preferably chosen from the group of such flavourings mentioned above.

Esters which are particularly preferred for increasing the solubility of 4-hydroxydihydrochalcones of the formula (I) or their salts or corresponding mixtures to be used according to the invention are chosen from the group consisting of ethyl lactate, n-propyl lactate, n-butyl lactate, diethyl tartrate, dimethyl succinate, diethyl succinate, dimethyl malonate, diethyl malonate, dimethyl malate, diethyl malate, and triethyl citrate as well as the solvent 1,2-propylene glycol.

Odour-providing, flavour-providing or taste-providing compositions according to the invention that contain the previously mentioned esters or solvents bring about very good solubility and inhibit any noticeable tendency towards recrystallisation of the 4-hydroxydihydrochalcones of the formula (I) or their salts and corresponding mixtures to be used according to the invention. They are therefore particularly suitable for incorporation into preparations according to the invention to be used for nutrition, oral hygiene or pleasure. Reference is made to the specifications given above with regard to preferred concentrations of the 4-hydroxydihydrochalcones or their salts in odour-providing, flavour-providing or taste-providing compositions according to the invention.

Preparations according to the invention that are used for nutrition, oral hygiene or pleasure are preferably produced by incorporating the 4-hydroxydihydrochalcones of the formula (I) or their salts or corresponding mixtures as such, as a solution (e.g. in ethanol, water, 1,2-propylene glycol, dimethylsulfoxide, optionally in the presence of one of the esters or solvents mentioned above) or in the form of a mixture with a solid or liquid supporting material (e.g. maltodextrin, starch, silica gel), flavours or flavour-providing substances and optionally further auxiliary agents and/or stabilisers (e.g. natural or artificial polysaccharides and/or plant gums such as modified starches or gum arabica), i.e. in the form of a semi-finished product, into a base preparation to be used for nutrition, oral hygiene or pleasure. Preparations according to the invention that are present as a solution and/or suspension can advantageously first be converted into a solid preparation according to the invention (semi-finished product) by spray-drying, before this is then used to produce the preparations to be used according to the invention for nutrition, oral hygiene or pleasure. Reference is made to the specifications given above with regard to the particular suitability of spray-dried semi-finished products for producing preparations to be used for nutrition, oral hygiene or pleasure.

In accordance with another preferred embodiment, for producing preparations according to the invention, the 4-hydroxydihydrochalcones of the formula (I) or their salts to be used according to the invention and optionally other constituents of the preparation according to the invention are first incorporated in emulsions, in liposomes, e.g. starting from phosphatidylcholine, in microspheres, in nanospheres or else in capsules, granules or extrudates made from a matrix suitable for foodstuffs and items consumed for pleasure, e.g. made from starch, starch derivatives (e.g. modified starch), cellulose or cellulose derivatives (e.g. hydroxypropylcellulose), other polysaccharides (e.g. dextrin, alginate, curdlan, carrageenan, chitin, chitosan, pullulan), natural fats, natural waxes (e.g. beeswax, carnauba wax), made from proteins, e.g. gelatine or other natural products (e.g. shellac). In doing so, depending on the matrix, the products can be obtained by spray-drying, spray-granulation, melt granulation, fluidised bed processes (e.g. in accordance with WO 97/16078 or WO 2004/022642), fluidised bed granulation (e.g. in accordance with WO 00/36931 or U.S. Pat. No. 4,946,654), coacervation, coagulation, extrusion, melt extrusion (e.g. in accordance with WO 2003/092412, EP 1 123 660 or EP 1 034 705), emulsion processes, coating or other suitable encapsulation processes and optionally a suitable combination of the previously mentioned processes. In another preferred method of production of a preparation according to the invention, the 4-hydroxydihydrochalcones or their salts to be used according to the invention are first complexed with one or more suitable complexing agents, for example with cyclodextrins or cyclodextrin derivatives, preferably, alpha- or beta-cyclodextrin, and used in this complexed form.

In some cases, a preparation according to the invention is preferred in which the matrix is chosen in such a way that the 4-hydroxydihydrochalcones of the formula (I) or their salts to be used according to the invention are released from the matrix after a delay, so that a long-lasting effect is produced. In such an event, a fat, wax, polysaccharide or protein matrix is particularly preferred.

Conventional basic materials, auxiliary agents and additives for foodstuffs and items consumed for pleasure may be used as further constituents of preparations according to the invention to be used for nutrition or items consumed for pleasure, e.g. water, mixtures of fresh or processed plant or animal basic materials or raw materials (e.g. raw, roasted, dried, fermented, smoked and/or boiled meat, bones, gristle, fish, vegetables, fruit, herbs, nuts, vegetable or fruit juices or pastes or mixtures of these), digestible or non-digestible carbohydrates (e.g. saccharose, maltose, fructose, glucose, dextrin, amylose, amylopectin, inulin, xylan, cellulose, tagatose), sugar alcohols (e.g. sorbitol, erythritol), natural or hardened fats (e.g. tallow, lard, palm oil, coconut oil, hardened plant oils), oils (e.g. sunflower oil, groundnut oil, corn seed oil, olive oil, fish oil, soya oil, sesame oil), fatty acids or their salts (e.g. potassium stearate), proteinogenic or non-proteinogenic amino acids and allied compounds (e.g. γ-aminobutyric acid, taurin), peptides (e.g. glutathione), native or processed proteins (e.g. gelatine), enzymes (e.g. peptidases), nucleic acids, nucleotides, taste correctors for unpleasant impressions of taste, other taste modulators for other, generally not unpleasant, impressions of taste, other taste-modulating substances (e.g. inositol phosphate, nucleotides such as guanosine monophosphate, adenosine monophosphate or other substances such as sodium glutamate or 2-phenoxypropionic acid), emulsifiers (e.g. lecithins, diacylglycerols, gum arabica), stabilisers (e.g. carrageenan, alginate), preservatives (e.g. benzoic acid, sorbic acid), antioxidants (e.g. tocopherol, ascorbic acid), chelators (e.g. citric acid), organic or inorganic acidifying agents (e.g. malic acid, acetic acid, citric acid, tartaric acid, phosphoric acid), bitter substances (e.g. quinine, caffeine, limonine, amarogentin, humolone, lupolone, catechol, tannins), mineral salts (e.g. sodium chloride, potassium chloride, magnesium chloride, sodium phosphates), enzymatic browning-preventative substances (e.g. sulfite, ascorbic acid), ethereal oils, plant extracts, natural or synthetic colorants or dye pigments (e.g. carotinoids, flavonoids, anthocyans, chlorophyll and their derivatives), spices, trigeminally active substances or plant extracts containing such trigeminally active substances, flavourings or odour-providing substances that are synthetic, natural or, identical to natural substances and odour correctors.

Dental care products (as an example of an oral care product according to the invention), that contain 4-hydroxydihydrochalcones of the formula (I) or their salts to be used according to the invention generally contain an abrasive system (grinding or polishing agent) such as e.g. silicas, calcium carbonate, calcium phosphate, aluminium oxide and/or hydroxylapatite, surface-active substances such as e.g. sodium lauryl sulfate, sodium lauryl sarcosinate and/or cocamidopropylbetain, moisture retainers such as e.g. glycerine and/or sorbitol, thickeners such as e.g. carboxymethylcellulose, polyethylene glycols, carrageenan and/or Laponite®, sweeteners such as e.g. saccharin, taste correctors for unpleasant impressions of taste, taste correctors for other, generally not unpleasant, impressions of taste, taste-modulating substances (e.g. inositol phosphate, nucleotides such as guanosine monophosphate, adenosine monophosphate or other substances such as sodium glutamate or 2-phenoxypropionic acid), cooling ingredients such as e.g. menthol, menthol derivatives (e.g. L-menthol, L-menthyl lactate, L-menthyl alkyl carbonates, menthone ketals, menthanecarboxamides), 2,2,2-trialkyl acetamides (e.g. 2,2-diisopropylpropionmethylamide), icilin and icilin derivatives, stabilisers and active ingredients such as e.g. sodium fluoride, sodium monofluorophosphate, tin difluoride, quaternary ammonium fluorides, zinc citrate, zinc sulfate, tin pyrophosphate, tin dichloride, mixtures of different pyrophosphates, triclosan, cetylpyridinium chloride, aluminium lactate, potassium citrate, potassium nitrate, potassium chloride, strontium chloride, hydrogen peroxide, flavours and/or sodium bicarbonate or odour correctors.

Chewing gums (as another example of preparations used for oral hygiene) that contain 4-hydroxydihydrochalcones of the formula (I) or their salts to be used according to the invention generally contain a chewing gum base, i.e. a chewable material that becomes plastic when chewed, sugars of various kinds, substitute sugar materials, other sweet-tasting substances, sugar alcohols, taste correctors for unpleasant impressions of taste, other taste modulators for, generally not unpleasant, impressions of taste, taste modulating substances (e.g. inositol phosphate, nucleotides such as guanosine monophosphate, adenosine monophosphate or other substances such as sodium glutamate or 2-phenoxypropionic acid), moisture retainers, thickeners, emulsifiers, flavours, and stabilisers or odour correctors.

A particularly preferred preparation according to the invention contains at least one other substance to mask or minimise a bitter, metallic, limey, acidic or astringent impression of taste or to enhance an impression of sweetness, saltiness or umami. Thus one or more 4-hydroxydihydrochalcones or their salts or corresponding mixtures to be used according to the invention are used in combination with at least one (other) substance suitable for masking an unpleasant (bitter, limey, acidic, astringent) impression of taste or to enhance a pleasant impression of taste (sweet, salty, umami). These special preparations are outstandingly suitable for achieving particularly effective enhancement of the sweetness in preparations according to the invention that contain sweet-tasting substances. The combination of 4-hydroxydihydrochalcones or their salts being used according to the invention and taste correctors for unpleasant, in particular bitter, impressions of taste, or taste enhancers for pleasant, in particular sweet, impressions of taste is particularly preferred.

Preparations according to the invention that contain hesperetin or its salts or corresponding mixtures are particularly preferred.

A particularly preferred combination is thus produced by the use of 4-hydroxydihydrochalcones of the formula (I) or their salts (particularly the $Na^+$, $K^+$, $NH_4^+$, $Ca^{2+}$, $Mg^{2+}$, $Al^{3+}$ and/or $Zn^{2+}$ salts) or corresponding mixtures, in particular by the use of phloretin (compound 4) or its salts together with hesperetin or its salts or corresponding mixtures for enhancing the sweetness of the sweet-tasting substances mentioned above, in particular sugars. Reference is also made here to U.S. Provisional Application 60/702,943 and the documents based thereon (Symrise) with regard to the sweetness-enhancing effect of hesperetin. The total concentration of 4-hydroxydihydrochalcones of the formula (I) or their salts or corresponding mixtures is then preferably at most 0.01 wt. % (100 ppm) and the total concentration of hesperetin or its salts or corresponding mixtures is preferably at most 0.01 wt. % (100 ppm), each with respect to the total weight of the preparation. The cited total concentrations here refer to ready-to-use preparations used for nutrition, oral hygiene or pleasure. Accordingly, the total concentration in semi-finished products, odour-providing, flavour-providing or taste-providing compositions is much higher. The ratio of the total amount of (i) 4-dydroxydihydrochalcones of the formula (I) and (ii) their salts to the total amount of hesperetin and its salts used is preferably in the range 1000:1 to 1:1000, preferably in the range 10:1 to 1:10, particularly preferably in the range 5:1 to 1:5, and very particularly preferably in the range 7:3 to 3:7.

Hesperetin has the following structural formula:

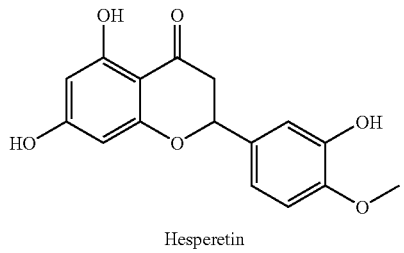 [SMILES: COc1ccc(C2CC(=O)c3c(O)cc(O)cc3O2)cc1O]

Hesperetin wherein hesperetin and/or its salts (in particular in the form of $Na^+$, $K^+$, $NH_4^+$, $Ca^{2+}$, $Mg^{2+}$, $Al^{3+}$ and/or $Zn^{2+}$ salts) may be present as the (2S)-enantiomer, (2R)-enantiomer or any mixture of the enantiomers, preferably in a mixture which contains equal parts of the enantiomers or in which the (2S)-enantiomer accounts for more than 50% of the total weight of the hesperetin enantiomers.

The (further) correctors are chosen e.g. from the following list: nucleotides (e.g. adenosine-5'-monophosphate, cytidine-5'-monophosphate) or their pharmaceutically acceptable salts, lactisoles, sodium salts (e.g. sodium chloride, sodium lactate, sodium citrate, sodium acetate, sodium gluconate), other hydroxyflavanones (e.g. eriodictyol, homoeriodictyol or their sodium salts), in particular in accordance with US 2002/0188019, hydroxybenzoic amides according to DE 10 2004 041 496 (e.g. 2,4-dihydroxybenzoic vanillylamide, 2,4-dihydroxybenzoic-N-(4-hydroxy-3-methoxybenzyl)amide, 2,4,6-trihydroxybenzoic-N-(4-hydroxy-3-methoxybenzyl)amide, 2-hydroxy-benzoic-N-4-(hydroxy-3-methoxybenzyl)amide, 4-hydroxybenzoic-N-(4-hydroxy-3-methoxybenzyl)amide, 2,4-dihydroxybenzoic-N-(4-hydroxy-3-methoxybenzyl)amide mono-sodium salt, 2,4-dihydroxybenzoic-N-2-(4-hydroxy-3-methoxyphenyl)ethylamide, 2,4-dihydroxybenzoic-N-(4-hydroxy-3-ethoxybenzyl)amide, 2,4-dihydroxybenzoic-N-(3,4-dihydroxybenzyl)amide and 2-hydroxy-5-methoxy-N-[2-(4-hydroxy-3-methoxyphenyl)ethyl]amide (aduncamide), 4-hydroxybenzoic vanillylamide), bitterness-masking hydroxydeoxybenzoins in accordance with U.S. Provisional Application 60/668,189 as well as the documents based thereon (Symrise) (e.g. 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl) ethanone, 1-(2-hydroxy-4-methoxyphenyl)-2-(4-hydroxy-3-methoxyphenyl)ethanone), amino acids (e.g. gamma-aminobutyric acid according to WO 2005/096841 for minimising or masking an unpleasant impression of taste such as bitterness), malic glycosides according to WO 2006/003107, salty-tasting mixtures in accordance with U.S. Provisional Application 60/728,744 as well as the documents based thereon (Symrise), diacetyl trimers in accordance with PCT/EP 2005/056355 as well as the documents based thereon (Symrise), mixtures of whey proteins with lecithins and/or bitter-masking substances such as gingerdione in accordance with U.S. Provisional Application 60/696,670 as well as the documents based thereon (Symrise).

It has already been specified several times that preparations according to the invention are chosen in particular from the group of preparations used for nutrition, oral hygiene or pleasure that consists of semi-finished products, odour-providing, flavour-providing or taste-providing compositions or mixtures of spices. Preferred preparations according to the invention are given below: baked goods (e.g. bread, biscuits, cakes, muffins, waffles, baking mixtures, other cakes and pastries), confectionery (e.g. white, pale or dark chocolates, filled chocolates, (for example filled with flavoured fondant materials, After-Eight types), chocolate bars, other bar products, chewable sweets, fruit gums, hard and soft toffees, chewing gum, sugar drops, lollipops), capsules (preferably seamless capsules for direct consumption, preferably with an outer covering based on gelatine and/or alginate), fatty materials (e.g. fillings for e.g. biscuit fillings, chocolate fatty fillings, bar fatty fillings), sprinkling mixtures (toppings), alcoholic or non-alcoholic drinks (e.g. coffee, tea, wine, wine-containing drinks, beer, beer-containing drinks, liqueurs, schnapps, brandy, fruit-containing fizzy drinks, isotonic drinks, soft drinks, crushed fruit drinks, fruit and vegetable juices with the exception of non-modified apple juice products, fruit or vegetable preparations), instant drinks or instant powders (e.g. instant cocoa drinks, instant tea drinks, instant coffee drinks, instant desserts in powdered form such as blancmange powders or jellies), meat products (e.g. ham, fresh sausage or raw sausage preparations, spiced or marinated fresh or salt meat products), eggs or egg products (e.g. dried egg powder), cereal products and/or nut products (e.g. breakfast cereals, cornflakes, oat flakes, bulk muesli, muesli bars, student food, sweet popcorn, nut bars, fruit-and-nut bars, pre-cooked ready-to-eat rice products), milk products (e.g. milk drinks, milk ice-cream, yoghurt, blancmange, kefir, fresh cheese, soft cheese, hard cheese, dried milk powder, whey, butter, buttermilk, partly or fully hydrolysed milk protein-containing products), products made from soya protein or other soya bean fractions (e.g. soya milk or other products made therefrom, soya lecithin-containing preparations, fermented products such as tofu or tempeh or products made therefrom, soy sauces), fruit preparations (e.g. jams, fruit ice-creams, fruit sauces, fruit fillings with the exception of natural apple products), vegetable preparations (e.g. ketchup, sauces, dried vegetable, deep-frozen vegetables, pre-cooked vegetables, vegetables stored in vinegar, preserved vegetables), nibbles (e.g. baked or fried potato crisps or potato dough products, bread dough products, extrudates based on maize or peanuts), products based on fats and oils or corresponding emulsions (e.g. mayonnaise, remoulade, dressings, spice preparations), other prepared dishes and soups (e.g. dried soups, instant soups, pre-cooked soups), spices, seasoning mixtures as well as in particular sprinkle-on seasonings that are used, for example in the snack sector.

Preparations according to the invention may also be presented as food supplements in the form of capsules, tablets (non-coated and coated tablets, e.g. gastric acid-resistant coatings), dragees, granules, pellets, solid mixtures, dispersions in liquid phases, as emulsions, as powders, as solutions, as pastes or as other swallowable or chewable preparations.

The present invention also provides a process for enhancing the sweet taste or the impression of a sweet smell of a flavouring that gives an impression of a sweet smell, using the following step:

Mixing one or more sweet-tasting substances (component (b)) or one or more flavourings that give an impression of a sweet smell (component (c)), with a total amount of a component (a) as defined above, i.e. with a total amount of a 4-hydroxydihydrochalcone of the formula (I) or a corresponding salt or a corresponding mixture, wherein the total amount of component (a) in the preparation is sufficient to enhance the impression of a sweet taste of the sweet-tasting substance(s) (b) or the impression of a sweet smell of the flavouring(s) (c) that give an impression of a sweet smell.

For the preferred amounts of the 4-hydroxydihydrochalcones of the formula (I) or their salts and corresponding mixtures to be used according to the invention, see above. A total amount of at least 1 ppm and at most 30 ppm in a ready-to-use preparation used for oral hygiene or a ready-to-eat preparation used for nutrition or items consumed for pleasure is often particularly preferred.

Also in the process according to the invention, the ratio of the total amount of (i) 4-hydroxydihydrochalcones of the formula (I) or their salts present in component (a) to the total amount of optionally used glycosides of (i) 4-hydroxydihydrochalcones of the formula (I) and (ii) their salts used in component (a) is preferably at least greater than 1:3, more preferably greater than 1:1, particularly preferably greater than 10:1.

The component (a) preferably comprises phloretin and in addition either (A) no phloridzin or (B) phloridzin, wherein the ratio of the amount of phloretin to the amount of phloridzin is greater than 1:3, preferably greater than 1:1, particularly preferably greater than 10:1, also in a process according to the invention.

Overall, however, the previous specifications cited with regard to the use according to the invention and to preparations according to the invention are also valid for the process according to the invention.

Finally, the present invention also provides the new compound 3-(4-hydroxy-3-methoxyphenyl)-1-(2,4,6-trihydroxyphenyl)propan-1-one (2',4,4',6'-tetrahydroxy-3-methoxydihydrochalcone; compound 8).

EXAMPLES

The examples are used to explain the invention without thereby restricting the invention. Unless stated otherwise, all data is with reference to weight.

Example 1

Phloretin, compound 4

A commercially available phloretin (Sigma-Aldrich, order no. P 7912, CA-No. 60-82-2, purity >98% was used.

Sensory profile of 30 ppm phloretin in 5 wt. % aqueous sugar solution (sucrose): sweet, astringent, dusty-dry Example 2

Synthesis of compound 5, 2',4-dihydroxy-3-methoxydihydrochalcone

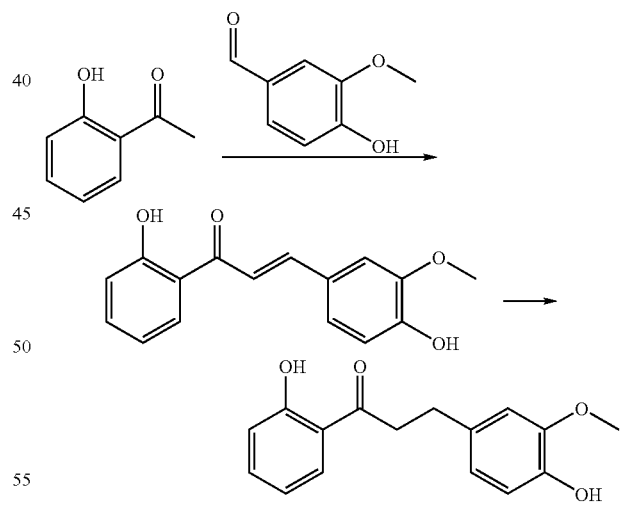

2-hydroxyacetophenone (6.8 g, 50 mmol) was condensed with vanillin (7.7 g, 50 mmol) in ethanol (100 ml) and piperidine (8.5 g) at room temperature (20° C.) under nitrogen for 4 days to give 2',4-dihydroxy-3-methoxychalcone. The crude mixture was filtered and the filter residue was washed with ethanol. The crude product (9.8 g) was stirred up with ethyl acetate and the intermediate product was filtered off (yield 8.3 g, 61% of theoretical). The intermediate product (2.73 g, 10 mmol) was then hydrogenated in ethanol (60 ml) using hydrogen at atmospheric pressure with the aid of a palladium catalyst on activated carbon (0.3 g, 10 wt. % Pd content, moist, water content ca. 50 wt. %), then filtered and the filtrate was evaporated to dryness, wherein compound 5 was obtained as a colourless crystalline material (2.3 g, purity >95%).

MS (EI): m/z=272 (60%, M), 137 (100%), 121 (52%), 65 (26%), 28 (25%), 151 (12%)

HPLCMS (APCI+): m/z=272.05 (20%), 269.29 (100%, [M−2+H]$^+$)

$^1$H-NMR (400 MHz, CDCl$_3$): δ=12.32 (1H, s, OH), 7.73 (1H, dd, J=8.1 Hz, J=1.7 Hz, H-6'), 7.45 (1H, ddd, J=8.5 Hz, J=7.2 Hz, J=1.7 Hz, H-4'), 6.98 (1H, ddd, J=8.4 Hz, J=1.13 Hz, J=0.4 Hz, H-3'), 6.87 (1H, ddd, J=8.1 Hz, J=7.2 Hz, J=1.2 Hz, H-5'), 6.84 (1H, dd, J=7.9 Hz, J=0.6 Hz, H-5), 6.74 (1H, m, H—H-2), 6.71 (1H, m, H-6), 3.86 (3H, s, O—CH$_3$), 3.29 (2H, m, H-α), 2.99 (2H, m, H-β) ppm.

$^{13}$C-NMR (100 MHz, CDCl$_3$): δ=205.68 (C, carbonyl-C), 162.43 (C, C-2'), 146.55 (C, C-3), 144.11 (C, C-4), 136.37 (CH, C-4'), 132.59 (C, C-1), 129.90 (CH, C-6'), 120.86 (CH, C-6), 119.32 (C, C-1'), 118.96 (CH, C-5'), 118.53 (CH, C-3'), 114.52 (CH, C-5), 111.18 (CH, C-2), 55.89 (CH$_3$, O—CH$_3$), 40.42 (CH$_2$, C-a), 29.86 (CH$_2$, C-β) ppm.

Sensory profile of 100 ppm 2',4-dihydroxy-3-methoxydihydrochalcone in 5 wt. %, aqueous sugar solution (sucrose): phenolic Example 3

Synthesis of compound 6, 2',4,4'-trihydroxy-3-methoxydihydrochalcone (3.6 g). The red crude product obtained was recrystallised from ethyl acetate, wherein compound 6 was obtained as a beige crystalline material (>95% purity).

HPLCMS (APCI−): m/z=287.29 (3.2%, [M-H]$^−$), 574.72 (100%, [2M-H]$^−$)

$^1$H-NMR (400 MHz, CD$_3$OD): δ=7.57 (1H, d, J=9.0 Hz, H-6'), 6.79 (1H, dd, J=1.9 Hz, J=0.3 Hz, H-2), 6.69 (1H, dd, J=8.0 Hz, J=1.9 Hz, H-5), 6.65 (1H, ddd, J=8.0 Hz, J=1.9 Hz, J=0.6 Hz, H-6), 6.21 (1H, dd, J=9.0 Hz, J=2.4 Hz, H-5'), 6.08 (1H, d, J=2.4 Hz, H-3'), 3.80 (3H, s, O—CH$_3$), 3.10 (2H, m, H-α), 2.91 (2H, m, H-β) ppm.

$^{13}$C-NMR (100 MHz, CD$_3$OD): δ=204.10 (C, carbonyl-C), 173.49 (C, C-2'), 167.13 (C, C-4'), 148.90 (C, C-3), 145.83 (C, C-4), 134.08 (C, C-1), 133.64 (CH, C-6'), 121.81 (CH, C-6), 116.19 (CH, C-5), 113.19 (CH, C-2), 112.29 (CH, C-5'), 111.79 (C, C-1'), 104.74 (CH, C-3'), 56.35 (CH$_3$, O—CH$_3$), 40.63 (CH$_2$, C-α), 32.24 (CH$_2$, C-β) ppm.

Sensory profile of 100 ppm 2',4,4'-trihydroxy-3-methoxy-dihydrochalcone in 5 wt. %, aqueous sugar solution (sucrose): neutral, slightly syrupy overtone Example 4

Synthesis of compound 8, 2',4,4',6'-tetrahydroxy-3-methoxydihydrochalcone

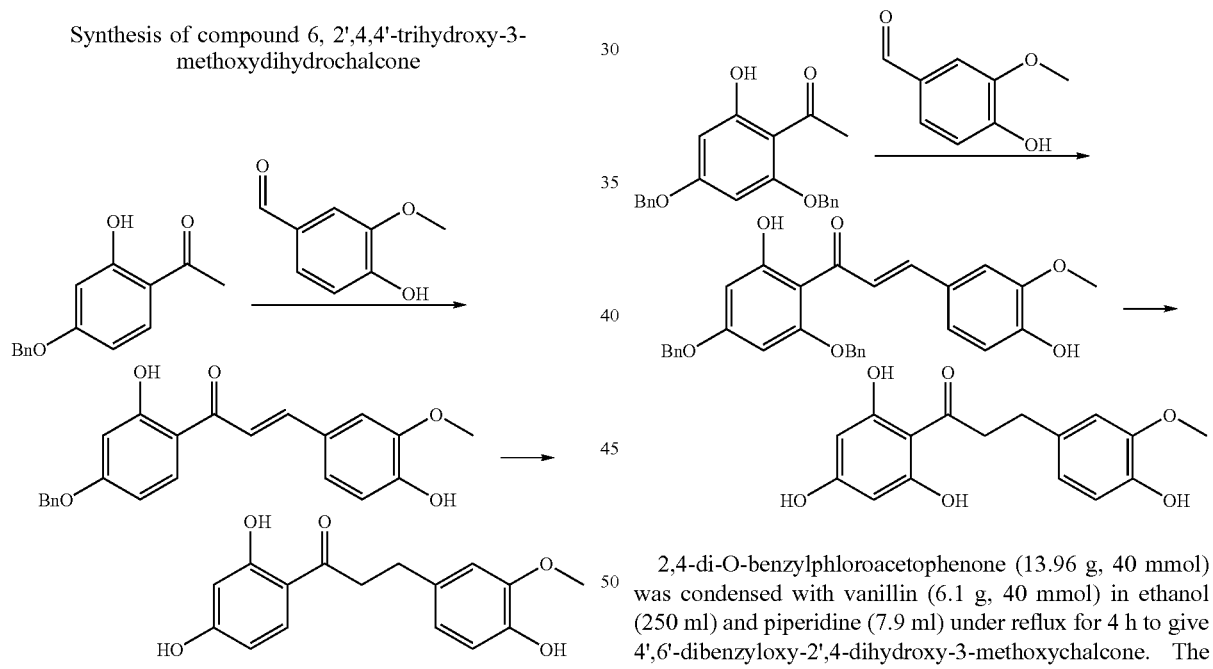

4-O-benzylphloroacetophenone (9.61 g, 40 mmol) was condensed with vanillin (6.1 g, 40 mmol) in ethanol (150 ml) and piperidine (8 ml) under reflux for 9.5 h to give 4'-Benzyloxy-2',4-dihydroxy-3-methoxychalcone and then water was added (300 ml). The first precipitate (dark red crystals) was filtered off, ethyl acetate was added to the filtrate and the product was crystallised with the aid of an ultrasonic bath (7.2 g, yellowy-brown crystalline material). The intermediate product (7.2 g, 19 mmol) was then hydrogenated in ethanol (200 ml) using hydrogen at atmospheric pressure and with the aid of a palladium catalyst on activated carbon (0.9 g, 10 wt. % Pd content, moist, water content ca. 50 wt. %), then filtered and the filtrate was evaporated to dryness 2,4-di-O-benzylphloroacetophenone (13.96 g, 40 mmol) was condensed with vanillin (6.1 g, 40 mmol) in ethanol (250 ml) and piperidine (7.9 ml) under reflux for 4 h to give 4',6'-dibenzyloxy-2',4-dihydroxy-3-methoxychalcone. The first precipitate was filtered off, the mother liquor was extracted again with diethyl ether after the addition of water and the organic phase was evaporated off. Ethyl acetate was added to the residue and this was crystallised with the aid of an ultrasonic bath. The second precipitate was filtered off and washed. From the combined precipitates of the intermediate product (7.1 g), 6.6 g (13.7 mmol) were then hydrogenated in ethanol (350 ml) using hydrogen at atmospheric pressure with the aid of a palladium catalyst on activated carbon (0.7 g, 10 wt. % Pd content, moist, water content ca. 50 wt. %), then filtered and the filtrate was evaporated to dryness (4.3 g, >90% purity). The crude product obtained was chromatographed on silica gel with ethyl acetate/methanol 100:1 (v/v) and then the evaporated eluate (4.7 g) was recrystallised from ethyl acetate, wherein compound 8 was obtained as a colourless crystalline material (1.53 g, >95% purity).

HPLCMS (APCI−): m/z=303.25 (100%, [M-H]$^+$), 606.63 (69%, [2M-H]$^+$)

$^1$H-NMR (400 MHz, CDCl$_3$): δ=12.23 (2H, bs, OH), 10.35 (1H, bs, OH), 8.67 (1H, bs, OH), 6.80 (1H, d, J=2 Hz, H-2), 6.67 (1H, d, J=8.0 Hz, H-5), 6.61 (1H, dd, J=8.0 Hz, J=2.0 Hz, H-6), 5.81 (2H, s, H-3+5) 3.74 (3H, s, O—CH$_3$), 3.24 (2H, m, H-α or H-β), 2.79 (2H, m, H-β or H-α) ppm.

$^{13}$C-NMR (100 MHz, CDCl$_3$): δ=204.17 (C, carbonyl-C), 164.51 (C, C-4'), 164.10 (2×C, C-2, C-6), 147.29 (C, C-3), 144.48 (C, C-4), 132.27 (C, C-1), 120.24 (CH, C-6), 115.21 (CH, C-5), 112.51 (CH, C-2), 103.64 (C, C-1'), 94.56 (2×CH, C-5', C-3'), 55.42 (CH$_3$, O—CH$_3$), 45.38 (CH$_2$, C-α), 29.88 (CH$_2$, C-β) ppm.

Sensory profile 100 ppm 2',4,4',6'-tetrahydroxy-3-methoxydihydrochalcone in 5 wt. %, aqueous sugar solution (sucrose): woody, balsamic Application Example 1

Enhancing the Impression of Sweetness of a Solution Containing a Sweet-Tasting Substance In order to quantify the enhancement of an impression of sweetness by adding 4-hydroxydihydrochalcones to be used according to the invention, the sweetness of a solution containing a sweet-tasting substance and of samples containing the same amount of sweet-tasting substance and in addition a certain concentration of the 4-hydroxydihydrochalcones of the formula (I) to be used according to the invention was determined by a group of experts (classification 0 [extremely weaklysweet] to 10 [extremely sweet]). Evaluation was performed by calculating the enhancement (in %) of the impression of sweetness from the average values of the ratings for the solution containing the sweet-tasting substance (a) and for the solution containing the sweet-tasting substance and 4-dydroxydihydrochalcones (b).

Application Example 2

Impression of Sweetness of a Sugar-Reduced Test Solution

In order to quantify the retention of an impression of sweetness when replacing a proportion of sucrose with a small amount of 4-hydroxydihydrochalcones of the formula (I) being used in accordance with the invention, the sweetness (a) of a solution containing 6 wt. % of sucrose as compared with a solution containing 5 wt. % of sucrose and (b) or (c) of a solution containing 6 wt. % of sucrose as compared with a solution containing 5% of sucrose and a certain concentration of a 4-hydroxydihydrochalcone being used according to the invention was determined by a group of experts (classification 0 [not sweet] to 10 [extremely sweet]). Evaluation was performed by calculating the enhancement (in %) of the impression of sweetness from the average values of the estimates for the solutions of 6% sucrose (second column) and for the solutions containing 5% sucrose and optionally the 4-hydroxydihydrochalcone of the formula (I) being used according to the invention (third column).

TABLE

Sweetness (a) of a 6 wt. % sucrose solution compared with a 5 wt. % sucrose solution, (b), (c) sweetness of a solution containing 6 wt. % sucrose compared with that of a solution containing 5 wt. % sucrose and the 4-hydroxydihydrochalcone of the formula (I) to be used according to the invention; the standard deviations are cited as the errors. In the last column, the numbers given in brackets indicate the total number of tasters against the number of tasters who felt that the test solution containing 5 wt. % of sucrose and optionally the 4-hydroxydihydrochalcone to be used according to the invention was sweeter than the test solution containing 6 wt. % of sucrose.

| Test | Impression of sweetness (1-10) | | % enhancement of the impression of sweetness |
|---|---|---|---|
| | 6% sucrose | 5% sucrose | |
| (a) | 6.9 ± 1.6 | 5.0 ± 1.6 | −30% (15/0) |

TABLE

Sweetness (a) of a solution containing a sweet-tasting substance and (b) a solution containing a sweet-tasting substance and a certain concentration of the 4-hydroxydihydrochalcone being used according to the invention; the standard deviations are cited as the errors. In the last column, the figures in brackets indicate the total number of tasters against the number of tasters who felt that test solution (b) was sweeter than test solution (a).

| Substance, concentration | Sweet-tasting substance, conc. | Impression of sweetness (1-10) | | % enhancement of the impression of sweetness |
|---|---|---|---|---|
| | | a) without | b) with | |
| Phloretin (compound 4), 30 ppm | Sucrose, 5% | 5.7 ± 1.4 | 7.4 ± 1.4 | +31% (16/14), p < 0.001 |
| Phloretin (compound 4), 30 ppm | Glycerine, 5% | 3.1 ± 1.5 | 4.4 ± 2.1 | +45% (16/11), p < 0.05 |
| 2',4-dihydroxy-3-methoxydihydrochalcone (compound 5), 100 ppm | Sucrose, 5% | 5 ± 1.8 | 6.2 ± 1.7 | +24% (16/13), p < 0.05+ 24% |
| 2',4,4',6'-tetrahydroxy-3-methoxydihydrochalcone (compound 8), 100 ppm | Sucrose, 5% | 5.3 ± 1.5 | 6.5 ± 1.4 | +23% (15/12), p < 0.05 |

TABLE-continued

Sweetness (a) of a 6 wt. % sucrose solution compared with a 5 wt. % sucrose solution, (b), (c) sweetness of a solution containing 6 wt. % sucrose compared with that of a solution containing 5 wt. % sucrose and the 4-hydroxydihydrochalcone of the formula (I) to be used according to the invention; the standard deviations are cited as the errors. In the last column, the numbers given in brackets indicate the total number of tasters against the number of tasters who felt that the test solution containing 5 wt. % of sucrose and optionally the 4-hydroxydihydrochalcone to be used according to the invention was sweeter than the test solution containing 6 wt. % of sucrose.

| Test | Impression of sweetness (1-10) | | % enhancement of the impression of sweetness |
|---|---|---|---|
| | 6% sucrose | 5% sucrose + 30 ppm phloretin (compound 4) | |
| (b) | 6.4 ± 1.6 | 6.1 ± 1.4 | −4.9% (16/7) |

TABLE-continued

Sweetness (a) of a 6 wt. % sucrose solution compared with a 5 wt. % sucrose solution, (b), (c) sweetness of a solution containing 6 wt. % sucrose compared with that of a solution containing 5 wt. % sucrose and the 4-hydroxydihydrochalcone of the formula (I) to be used according to the invention; the standard deviations are cited as the errors. In the last column, the numbers given in brackets indicate the total number of tasters against the number of tasters who felt that the test solution containing 5 wt. % of sucrose and optionally the 4-hydroxydihydrochalcone to be used according to the invention was sweeter than the test solution containing 6 wt. % of sucrose.

| Test | Impression of sweetness (1-10) | | % enhancement of the impression of sweetness |
|---|---|---|---|
| | 6% sucrose | 5% sucrose + 100 ppm 2',4,4',6'-tetrahydroxy-3-methoxydihydrochalcone (compound 8) | |
| (c) | 5.5 ± 1.2 | 4.9 ± 1.3 | −11% (15/4) |

Application Example 3

Spray-Dried Preparations as Semi-Finished Products for Flavouring Finished Products

| Ingredients | Preparation (amount used in wt. %) | | | | | | |
|---|---|---|---|---|---|---|---|
| | A | B | C | D | E | F | G |
| Drinking water | 60.8% | 60.8% | 60.8% | 60.8% | 60.8% | 60.8% | 60.8% |
| Maltodextrin from wheat | 24.3% | 24.3% | 24.3% | 24.3% | 24.3% | 24.3% | 24.3% |
| Gum arabica | 6.1% | 6.1% | 6.1% | 6.1% | 6.1% | 6.1% | 6.1% |
| Phloretin (compound 4) | 8.8% | — | — | 4.4% | 2.2% | 4.4% | — |
| 2',4-dihydroxy-3-methoxydihydrochalcone (compound 5) | — | 8.8% | — | — | — | — | — |
| 2',4,4'-trihydroxy-3-methoxydihydrochalcone (compound 6) | — | — | — | — | — | 4.4% | — |
| 2',4,4',6'-tetrahydroxy-3-methoxydihydrochalcone (compound 8) | — | — | 8.8% | — | 2.2% | — | 4.4% |
| Hesperetin | — | — | — | 4.4% | 4.4% | — | 4.4% |

The drinking water is initially introduced into a container and the maltodextrin and gum arabica are dissolved therein. Then the 4-hydroxydihydrochalcones being used according to the invention and the other constituents are emulsified in the supporting solution described above using a mixer (Turrax). The temperature of the resulting mixture should not exceed 30° C. The mixture is then spray-dried (set temperature at inlet: 185-195° C., set temperature at outlet: 70-75° C.). The spray-dried semi-finished product contains about 18-22% of the 4-hydroxydihydrochalcones of the formula (I) being used according to the invention.

Spray-dried preparations with other 4-hydroxydihydrochalcones being used according to the invention may also be produced in the same way.

Application Example 4

A Spray-Dried Preparation as a Semi-Finished Product for Flavouring Finished Products Using Further Sweetness-Modulating Substances

| Ingredients | Preparation (amount used in wt. %) | | | | | | | |
|---|---|---|---|---|---|---|---|---|
| | A | B | C | D | E | F | G | H |
| Drinking water | 60.8 | 60.8 | 60.8 | 60.8 | 60.8 | 60.8 | 60.8 | 60.8 |
| Maltodextrin from wheat | 24.3 | 24.3 | 24.3 | 24.3 | 24.3 | 24.3 | 24.3 | 24.3 |
| Gum arabica | 6.1 | 6.1 | 6.1 | 6.1 | 6.1 | 6.1 | 6.1 | 6.1 |
| Phloretin (compound 4) | 4.4 | | | 6.4 | 3.2 | 4.4 | 4.4 | 4.4 |
| 2',4-dihydroxy-3-methoxydihydrochalcone (compound 5) | | 4.4 | | | | | | |
| 2',4,4'-trihydroxy-3-methoxydihydrochalcone (compound 6) | | | | | | | | |
| 2',4,4',6'-tetrahydroxy-3-methoxydihydrochalcone (compound 8) | | | 6.4 | | 3.2 | | | |
| Gamma-aminobutyric acid | 4.4 | 4.4 | 2.4 | | | | | |
| Homoeriodictyol | | | | 2.4 | 2.4 | | | |
| Divanillin | | | | | | 4.4 | | |
| 2,4-dihydroxybenzoic-N-(4-hydroxy-3-methoxybenzyl)amide | | | | | | | 2.2 | |
| 6-(4-hydroxy-3-methoxyphenyl)-hexane-2,4-dione | | | | | | | 2.2 | |
| Diacetyl trimer of the formula | | | | | | | | 4.4 |

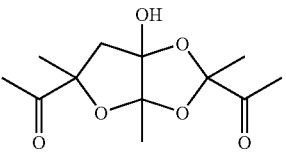 [SMILES: CC(=O)C1(C)CC2(O)OC(C)(C(C)=O)OC2(C)O1]

The drinking water is initially introduced into a container and the maltodextrin and gum arabica are dissolved therein. Then the flavourings are emulsified in the supporting solution using a mixer (Turrax). The temperature of the resulting mixture should not exceed 30° C. The mixture is then spray-dried (set temperature at the inlet: 185-195° C., set temperature at the outlet: 70-75° C.). The spray-dried semi-finished product contains about 18-22% of flavouring.

Application Example 5

Combinations with Sweet-Tasting Substances as Sweeteners

| Ingredients | Preparation (amount used in wt. %) | | | | | | | |
|---|---|---|---|---|---|---|---|---|
| | A | B | C | D | E | F | G | H |
| Sucrose | 89.9 | 89.9 | 89.9 | 89.9 | 89.9 | | | 50 |
| Fructose | 10 | 10 | 10 | | | | | |
| Tagatose | | | | 10 | 10 | | | |
| High Fructose Corn Syrup | | | | | | 99.9 | | |
| Maltitol | | | | | | | 99 | |
| Sorbitol | | | | | | | | 49.95 |
| Phloretin (compound 4) | 0.1 | 0.05 | 0.05 | | | | 0.05 | 0.025 |
| Hesperetin | | 0.05 | | | | | 0.05 | 0.025 |
| 2',4,4',6'-tetrahydroxy-3-methoxydihydrochalcone (compound 8) | | | 0.05 | | | | | |
| Phloretin (compound 4) as a spray-dried preparation (preparation A from application example 3) | | | | 0.5 | 0.25 | | 1 | |

-continued

| Ingredients | Preparation (amount used in wt. %) | | | | | | | |
|---|---|---|---|---|---|---|---|---|
| | A | B | C | D | E | F | G | H |
| 2',4,4',6'-tetrahydroxy-3-methoxydihydrochalcone (compound 8) as a spray-dried preparation (preparation C from application example 3) | | | | | 0.25 | | | |

The ingredients are mixed in the sequence given above. The resulting product can be used as sweetening agents for foods or items consumed for pleasure, e.g. in coffee or tea.

As an example of an application, tea and the product are mixed and packed into teabags made of filter paper. To use, 100-250 ml of boiling water is poured onto a teabag and allowed to infuse for 2-5 min.

Application Example 6

Flavouring Mixtures for Enhancing Sweetness

| Ingredients | Preparation (amount used in wt. %) | | | | | | | | | |
|---|---|---|---|---|---|---|---|---|---|---|
| | A | B | C | D | E | F | G | H | I | J |
| Vanilla flavouring (e.g. obtainable from Symrise) | 75.00 | | 75.00 | | | | | | | |
| Sugar flavouring, black treacle type | | 2.00 | | | | | | | | |
| Ethyl lactate | | | | 1.00 | 0.50 | 0.050 | | 0.50 | 1.00 | 0.05 |
| n-Propyl lactate | | | | 0.50 | | | | 0.50 | 0.50 | |
| n-Butyl lactate | | | | 0.30 | 0.30 | 0.030 | 1.80 | 0.30 | 0.30 | 0.03 |
| Diethyl malate | | | | 1.00 | | | 1.00 | 0.50 | 1.00 | |
| Diethyl tartrate | | | | 0.50 | | | | 0.50 | 0.50 | |
| Diethyl succinate | | | | 0.50 | | | | | 0.50 | 10.0 |
| Diethyl malonate | | | | 0.50 | | | 2.00 | | 0.50 | |
| Triethyl citrate | | | | 0.50 | | | | 0.50 | 0.50 | |
| Lactic acid | | | | 1.00 | 2.00 | 0.20 | 2.00 | | 2.00 | 0.20 |
| Hesperetin | | 0.30 | | | 1.25 | | 1.25 | | 0.50 | 2.50 |
| Phloretin (compound 4) | 0.625 | | 0.325 | 2.50 | 1.25 | 2.50 | 1.25 | 5.00 | 1.00 | 2.50 |
| 2',4,4',6'-tetrahydroxy-3-methoxydihydro-chalcone (compound 8) | | 2.45 | | | | | | | 1.00 | |
| 1,2-propylene glycol | to make up to 100 | to make up to 100 | to make up to 100 | to make up to 100 | to make up to 100 | to make up to 100 | to make up to 100 | to make up to 100 | to make up to 100 | to make up to 100 |

The components cited in the table are mixed in the sequence given, with stirring, and optionally fully homogenised by heating to 20-50° C. Clear, mostly colourless or yellowy solutions that can be used as flavourings are obtained.

Application Example 7

Chewing Gums

Application Example 7a

| Part | Ingredients | Amount used in wt. % |
|---|---|---|
| A | Chewing gum base, "Jagum T" Company | 30.00 |
| B | Sorbitol, powdered | 39.00 |
| | Isomalt ® (Palatinit GmbH) | 9.50 |

-continued

| Part | Ingredients | Amount used in wt. % |
|---|---|---|
| | Xylitol | 2.00 |
| | Mannitol | 3.00 |
| | Aspartame ® | 0.10 |
| | Acesulfam ® K | 0.10 |
| | Emulgum ® (Colloides Naturels, Inc.) | 0.30 |
| C | Sorbitol, 70% aqueous solution | 14.00 |
| | Glycerine | 1.00 |
| D | Spearmint flavouring, containing 1 wt. % of phloretin (compound 4), with respect to the total weight of flavouring | 1.00 |

Parts A to D are mixed and kneaded intensively. The crude material can be processed to give ready-to-chew chewing gum, e.g. in the form of thin strips.

Application Example 7b

Non-Stick Chewing Gum

Chewing gum base K1 consists of 2.0% butyl rubber (an isobutene/isoprene copolymer, MW 400000), 6.0% polyisobutene (MW=43800), 43.5% polyvinylacetate (MW=12000), 31.5% polyvinylacetate (MW=47000), 6.75% triacetin and 10.25% calcium carbonate. Chewing gum base K1 and the chewing gum can be produced in the same way as described in U.S. Pat. No. 5,601,858.

| | I (wt. %) | II (wt. %) | III (wt. %) |
|---|---|---|---|
| Chewing gum base K1 | 26.00 | 26.00 | 26.00 |
| Triacetin | 0.25 | 0.25 | 0.25 |
| Lecithin | 0.50 | 0.50 | 0.50 |
| Sorbitol, crystalline | 40.90 | 40.60 | 40.50 |
| Mannitol | 15.30 | 15.20 | 15.10 |
| Glycerine | 12.10 | 12.00 | 11.80 |
| Aspartame | 0.17 | 0.17 | 0.17 |
| Encapsulated aspartame | 1.08 | 1.08 | 1.08 |
| Amorphous silica | 1.00 | 1.00 | 1.00 |
| Cotton seed oil | 0.50 | 0.50 | 0.50 |
| Polyoxyethylene-sorbitane-monolaurate (E-432) | 1.00 | 1.00 | 1.00 |
| Encapsulated spearmint flavour (contains L-carvone) | 0.20 | 0.10 | 0.30 |
| Encapsulated wintergreen flavour (contains methyl salicylate) | — | 0.40 | — |
| Peppermint oil, containing 1 wt. % phloretin (compound 4), with respect to the total weight of flavouring | 1.00 | 1.20 | 1.50 |
| L-menthyl-L-lactate | 0.10 | — | 0.30 |

Application Example 7c

Bubble Gum

Bubble gum can be produced in the same way as described in U.S. Pat. No. 5,093,136.

| | I (wt. %) | II (wt. %) |
|---|---|---|
| Styrene/butadiene-copolymer (SBR) | 19.50 | 17.50 |
| Polyisobutene | 8.00 | 8.00 |
| Sorbitol powder | 49.19 | 47.19 |
| Sorbitol, 70%, in water | 9.20 | 22.20 |
| Hydrogenated starch hydrolysate (HSH) | 9.00 | — |
| Glycerine | 3.00 | 2.00 |
| Aspartame | 0.10 | 0.10 |
| Encapsulated aspartame | 0.50 | 0.50 |
| Red and blue colorants | 0.01 | 0.01 |
| Strawberry/raspberry flavouring containing 1 wt. % phloretin (compound 4), with respect to the total weight of flavouring | 1.50 | 2.50 |

The chewing gum in formulation (I) was shaped into compact balls, that in formulation (II) was shaped into hollow spheres.

Application Example 7d

Chewing Gum

Chewing gum base K2 consists of 28.5% terpene resin, 33.9% polyvinylacetate (MW=14000), 16.25% hydrogenated plant oil, 5.5% mono- and diglycerides, 0.5% polyisobutene (MW 75000), 2.0% butyl rubber (isobutene/isoprene copolymer), 4.6% amorphous silicon dioxide (water content ca. 2.5%), 0.05% antioxidant tert.-butylhydroxytoluene (BHT), 0.2% lecithin, and 8.5% calcium carbonate. The chewing gum base K2 and the chewing gum can be produced in the same way as described in U.S. Pat. No. 6,986,907.

| | I (wt. %) | II (wt. %) | III (wt. %) |
|---|---|---|---|
| Chewing gum base K2 | 25.30 | 27.30 | 26.30 |
| Sorbitol | 61.48 | 59.48 | 61.60 |
| Glycerine | 2.40 | 2.40 | 2.40 |
| Lecithin | 7.00 | 7.00 | 7.00 |
| Aspartame | 0.14 | 0.14 | 0.14 |
| Encapsulated aspartame | 0.68 | 0.68 | 0.48 |
| Menthol, spray-dried | 1.00 | 0.50 | 0.40 |
| Cherry flavouring, spray-dried | — | 1.20 | — |
| Lemon flavouring, containing 1 wt. % phloretin (compound 4), with respect to the total weight of flavouring | 1.20 | 1.30 | 1.68 |
| Orange oil, natural | 0.80 | — | — |

The chewing gums in formulations (I) and (II) were shaped into strips, that in formulation (III) was shaped into pellets.

Application Example 8

Toothpaste

| Part | Ingredients | Amount used in wt. % |
|---|---|---|
| A | Demineralised water | 22.00 |
| | Sorbitol, 70% aqueous solution | 45.00 |
| | Solbrol ® M, sodium salt (Bayer AG, alkyl p-hydroxybenzoate) | 0.15 |
| | Trisodium phosphate | 0.10 |
| | Saccharin, 450 specialist | 0.20 |
| | Sodium monofluorophosphate | 1.12 |
| | Polyethylene glycol 1500 | 5.00 |
| B | Sident 9 (abrasive silicon dioxide) | 10.00 |
| | Sident 22 S (thickening silicon dioxide) | 8.00 |
| | Sodium carboxymethylcellulose | 0.90 |
| | Titanium dioxide | 0.50 |
| C | Demineralised water | 4.53 |
| | Sodium lauryl sulfate | 1.50 |
| D | Peppermint flavouring, containing 1 wt. % phloretin (compound 4), with respect to the total weight of flavouring | 1.00 |

The ingredients in parts A and B were each premixed and then stirred thoroughly together under vacuum at 25-30° C. for 30 min. Part C was premixed and added to A and B; D is added and the mixture is stirred thoroughly under vacuum at 25-30° C. for 30 min. After releasing the vacuum, the toothpaste is ready and can be packaged.

Application Example 9

Sugar-Reduced Soft Drinks

Comparison preparation with normal sucrose content (A)
Comparison preparation with reduced sucrose content (B)
Preparations according to the invention (C-H)

| Ingredients | Preparation (amount used in wt. %) | | | | | | | |
|---|---|---|---|---|---|---|---|---|
| | A | B | C | D | E | F | G | H |
| Water | 89.85 | 91.85 | 91.797 | 91.797 | 91.299 | 91.599 | 91.499 | |
| Sucrose | 10.0 | 8.0 | 8.0 | 8.0 | 8.0 | 8.0 | 8.0 | 8.0 |
| Citric acid | 0.15 | 0.2 | 0.2 | 0.2 | 0.2 | 0.2 | 0.2 | 0.2 |
| Fructose | | | | | | 0.2 | | |
| Tagatose | | | | | | | 0.3 | |
| Maltitol syrup | | | | | 0.5 | | | |
| Erythritol | | | | | | | | 0.5 |
| Phloretin (Compound 4) | — | — | 0.003 | 0.0015 | 0.0005 | 0.0005 | 0.001 | 0.0005 |
| Hesperetin | — | — | — | 0.0015 | 0.0005 | 0.0005 | | 0.0005 |

The substances were initially introduced, made up with water and dissolved. Some of the tasting results (classification 0 [not sweet] to 10 [extremely sweet]) are given in the table below:

| Preparation | Impression of sweetness (1-10) | Enhancement/reduction |
|---|---|---|
| A (normal sucrose content) | 6.3 ± 1.6 | — |
| B (reduced sucrose content) | 4.0 ± 1.5 | B against A: −31% |
| C (reduced sucrose content + 30 ppm phloretin) | 6.3 ± 1.3 | C against A: 0%<br>C against B: +37% |

With preparation C, which also had a higher acidic fraction, the sweetness of the 10% sucrose-containing comparison preparation A could be achieved.

For preparation C, when compared to comparison preparation B, an even more substantially intense sweetness was perceptible.

Application Example 10

Use in a Sugar-Reduced Soft Drink Together with Other Flavourings and Taste-Providing Substances

| Ingredients | Conc. | Preparation | | | | | | | |
|---|---|---|---|---|---|---|---|---|---|
| | | A | B | C | D | E | F | G | H |
| Saccharose | % | 8 | 8 | 8 | 8 | 8 | 8 | 8 | 8 |
| Citric acid | % | 0.2 | 0.2 | 0.2 | 0.2 | 0.2 | 0.2 | 0.2 | 0.2 |
| Hesperetin 1% in 1,2-propylene glycol | % | 0.05 | 0.05 | 0.05 | 0.05 | 0.05 | 0.05 | 0.05 | 0.05 |
| Phloretin (compound 4) 1% in 1,2-propylene glycol | % | 0.05 | 0.05 | 0.05 | 0.05 | 0.1 | 0.1 | 0.1 | 0.15 |
| Ethylhydroxymethyl-furanone | ppb | 0.01 | | | | | | | |
| Vanillin | ppb | 15 | | | | | | | |
| Diethyl malonate | ppb | | 70 | | | | | | |
| Phenylethyl acetate | ppb | | 1 | | | | | | |
| 2-methylbutanal | ppb | | | 0.3 | | 0.3 | | | |
| Isovaleraldehyde | ppb | | | 0.2 | | 0.2 | | | |
| Furfuryl acetate | ppb | | | 0.3 | | | | | |
| Massoilactone | ppb | | | | 5 | 5 | | 5 | 5 |
| γ-octalactone | ppb | | | | 5 | 5 | | 5 | 5 |
| Ethyl butyrate | ppb | | | 0.5 | | 0.5 | | 0.5 | |
| Maltol | ppb | 350 | | | | 350 | | 350 | |
| 2,5-dimethyl-4-hydroxy-2H-furan-3-one | ppb | 3 | | | | 3 | | 3 | |
| Ethyl isobutyrate | ppb | | 0.1 | | | 0.1 | | 0.1 | |
| Ethyl-2-methylbutyrate | ppb | | 0.1 | | | 0.1 | | 0.1 | |
| 1,2-propylene glycol | % | 0.1 | 0.1 | 0.1 | 0.1 | 0.1 | 0.1 | 0.1 | 0.1 |
| Butylphenyl acetate | ppb | | | | | 10 | | | |
| Acetanisol | ppb | | | | | 20 | | | |
| Methyl sorbate | ppb | | | | | 100 | | | |
| L-lysine | ppm | | | | | | 100 | 30 | |
| Malic acid | ppm | | | | | | 80 | | |
| L-arginine | ppm | | | | | | 5 | 20 | |
| L-aspartic acid | ppm | | | | | | 0.5 | | |
| Calcium chloride | ppm | | | | | | 20 | | |
| Glutamine | ppm | | | | | | 2 | | |
| Potassium hydrogen phosphate | ppm | | | | | | 6 | | |
| Magnesium chloride | ppm | | | | | | 20 | | |
| L-valine | ppm | | | | | | 0.5 | | |
| Glycine | ppm | | | | | | | 40 | |
| L-alanine | ppm | | | | | | | 20 | |
| L-serine | ppm | | | | | | | 50 | |
| Water | | to make up to 100% | | | | | | | |

The substances were initially introduced and then made up to 100% with water and dissolved. The product was packaged in bottles if so required and carbonated.

Application Example 11

Sugar-Free Hard Toffee

| Ingredients | Conc. (%) |
|---|---|
| Palatinite, Type M | 75.10% |
| Water | 24.82% |
| Peppermint flavouring | 0.1% |
| Phloretin (compound 4) | 0.01% |

Palatinite was mixed with water and the mixture was melted at 165° C. and then cooled to 115° C. The peppermint flavouring and phloretin were added and after mixing thoroughly, the mixture was cast in moulds, removed from the moulds after solidification and then packaged individually.

Application Example 12

Sugar-Reduced Ready-Made Desserts

Comparison preparation with normal sucrose content (A)
Comparison preparation with reduced sucrose content (B)
Preparation according to the invention with reduced sucrose content and phloretin (compound 4) (C)
Preparation according to the invention with reduced sucrose content, D-tagatose and phloretin (compound 4) (D)

| | Preparation (data in wt. %) | | | |
|---|---|---|---|---|
| Ingredients | A | B | C | D |
| Sucrose | 7.8% | 5.4% | 5.4% | 5.4% |
| Starch | 3.0% | 3.0% | 3.0% | 3.0% |
| Skimmed milk powder | 1.5% | 1.5% | 1.5% | 1.5% |
| Aubygel MR50 | 0.5% | 0.5% | 0.5% | 0.5% |
| Vanilla pod extract, spray-dried, Symrise | 0.1% | 0.1% | 0.1% | 0.1% |
| Phloretin (compound 4) | — | — | 0.003% | 0.003% |
| D-tagatose | — | — | — | 0.1% |
| Milk 1.5% fat content | to make up to 100% | to make up to 100% | to make up to 100% | to make up to 100% |

The solid substances were initially introduced and stirred up with the milk. The mixture was heated to 95° C. for 2 min, with intensive stirring, packaged and cooled to 5-8° C.

With preparation C, when tasted by test people, the sweetness of the 7.8% sucrose-containing comparison preparation A could be achieved with a somewhat delayed impression of sweetness. Preparation C was substantially sweeter than comparison preparation B. Preparation D was comparable to C, but exhibited an improved initial sweetness.

Application Example 13

Low-Fat Yoghurts

Comparison preparation with sugar (A)
Preparations according to the invention with a mixture of sweeteners and 4-hydroxydihydrochalcones (B-D)

| | Preparation (data in wt. %) | | | |
|---|---|---|---|---|
| Ingredients | A | B | C | D |
| Sucrose | 10% | 8% | 7% | 6% |
| Tagatose | — | — | — | 0.5% |
| Fructose | — | — | — | 0.5% |
| Phloretin (compound 4) | — | 0.01% | — | 0.005% |
| 2',4,4',6'-tetrahydroxy-3-methoxydihydro-chalcone (compound 8) | — | — | 0.01% | — |
| Hesperetin | — | — | — | 0.005% |
| Yoghurt, 0.1% fat | to make up to 100% | to make up to 100% | to make up to 100% | to make up to 100% |

The ingredients were mixed and cooled to 5° C.

Application Example 14

Use Together with Sweeteners in Low-Fat Yoghurts

Comparison preparation with a mixture of sweeteners (A)
Preparations according to the invention with a mixture of sweeteners and 4-hydroxydihydrochalcones (B-D)

| | Preparation (data in wt. %) | | | |
|---|---|---|---|---|
| Ingredients | A | B | C | D |
| D-Tagatose | 0.482% | 0.482% | 0.482% | 0.482% |
| Sucralose | 0.003% | 0.003% | 0.003% | 0.003% |
| Aspartame | 0.005% | 0.005% | 0.005% | 0.005% |
| Acesulfam K | 0.01% | 0.01% | 0.01% | 0.01% |
| Phloretin (Compound 4) | — | 0.01% | — | 0.005% |
| 2',4,4',6'-tetrahydroxy-3-methoxydihydro-chalcone (compound 8) | — | — | 0.01% | — |
| Hesperetin | — | — | — | 0.005% |
| Yoghurt, 0.1% fat | to make up to 100% | to make up to 100% | to make up to 100% | to make up to 100% |

The ingredients were mixed and cooled to 5° C.

Application Example 15

Milk Shakes

Comparison preparations with sugar (A-B)
Preparations according to the invention with sugar and 4 hydroxydihydrochalcones (C-E)

| | Preparation (data in wt. %) | | | | |
|---|---|---|---|---|---|
| Ingredients | A | B | C | D | E |
| Sucrose | 10.0 | 8.0 | 8.0 | 8.0 | 7.0 |
| Fructose | — | — | — | — | 0.5 |
| Tagatose | — | — | — | — | 0.5 |
| Phloretin (compound 4) | — | — | 0.01% | — | 0.005% |
| 2',4,4',6'-tetrahydroxy-3-methoxydihydro-chalcone (compound 8) | — | — | — | 0.01% | — |

-continued

| Ingredients | Preparation (data in wt. %) | | | | |
|---|---|---|---|---|---|
| | A | B | C | D | E |
| Hesperetin | — | — | — | — | 0.005% |
| UHT-milk, 1.5% fat | to make up to 100% | | | | |

The ingredients were mixed, made up with milk, stirred well, placed in bottles and stored cool at 5° C.

Application Example 16

Sugar-Reduced Tomato Ketchup

Comparison preparation with sugar (A)
Comparison preparation with reduced sugar content (B)
Preparations according to the invention with sugar and 4-hydroxydihydrochalcones (C-I)

| Ingredients | Preparation (data in wt. %) | | | | | | | |
|---|---|---|---|---|---|---|---|---|
| | A | B | C | E | F | G | H | I |
| Common salt | 2 | 2 | 2 | 2 | 2 | 2 | 2 | 2 |
| Starch, Farinex WM 55 | 1 | 1 | 1 | 1 | 1 | 1 | 1 | 1 |
| Sucrose | 12 | 9.6 | 9.2 | 8.4 | 9.6 | 9.6 | 8.4 | 8.4 |
| Tomato concentrate 2-fold | 40 | 40 | 40 | 40 | 30 | 30 | 30 | 30 |
| Glucose syrup 80 Brix | 18 | 18 | 18 | 18 | 18 | 18 | 18 | 18 |
| Sprits vinegar 10% | 7 | 7 | 7 | 7 | 3 | 3 | 3 | 3 |
| Water | 20 | 22.4 | 22.4 | 23.2 | 36.0 | 36.0 | 37.2 | 37.2 |
| Phloretin (compound 4) 2.5% in 1,2-propylene glycol | | 0.4 | 0.2 | 0.2 | 0.4 | 0.2 | 0.2 | |
| 2',4,4',6'-tetrahydroxy-3-methoxydihydrochalcone (compound 8) 2.5% in 1,2-propylene glycol | | | | | | 0.2 | | |
| Hesperetin 2.5% in 1,2-propylene glycol | | | 0.2 | 0.2 | | | | 0.2 |

The ingredients are mixed in the sequence given above and the final ketchup is homogenised using an agitator, placed in bottles and sterilised.

Application Example 17

Sugar-Reduced Ice-Cream

Comparison preparation with sugar (A)
Comparison preparation with reduced sugar content (B)
Preparations according to the invention with sugar and 4-hydroxydihydrochalcones (C-F)

| Ingredients | Preparation (conc. in wt. %) | | | | | |
|---|---|---|---|---|---|---|
| | A | B | C | D | E | F |
| Skimmed milk | 57.15 | 61.15 | 60.95 | 61.05 | 60.95 | 61.05 |
| Plant fat, melting range 35-40 ° C. | 20.00 | 20.00 | 20.00 | 20.00 | 20.00 | 20.00 |
| Sugar (saccharose) | 12.00 | 8.00 | 8.00 | 8.00 | 8.00 | 8.00 |
| Skimmed milk powder | 5.00 | 5.00 | 5.00 | 5.00 | 5.00 | 5.00 |
| Glucose syrup 72% dry material | 5.00 | 5.00 | 5.00 | 5.00 | 5.00 | 5.00 |
| Emulsifier SE 30 (Grindstedt Products, Denmark) | 0.65 | 0.65 | 0.65 | 0.65 | 0.65 | 0.65 |
| Flavouring containing 0.1% diacetyl and 1% vanillin | 0.20 | 0.20 | 0.20 | 0.20 | | |
| Flavouring containing 0.1% diacetyl trimer (formula, see application example 4), 0.1% diacetyl and 1% vanillin | | | | | 0.20 | 0.20 |
| Flavouring according to application example 6, Preparation E | | | 0.20 | | 0.20 | |
| Flavouring according to application example 6, preparation H | | | | 0.10 | | 0.10 |

The skimmed milk and glucose syrup were heated to 55° and the sugar, skimmed milk powder and emulsifier were added. The plant fat was preheated and the entire mixture heated to 58° C. After adding the flavouring, the mixture was homogenised with the aid of a continuous-flow high-pressure homogeniser (180/50 bar). The material obtained was conditioned for 1 min at 78° C., then cooled to 2-4° C. and incubated at this temperature for 10 h to mature. Then the matured material was packaged and stored frozen at −18° C.

Application Example 18

Ice-Cream Suitable for Diabetics

An ice-cream suitable for diabetics was produced from the following ingredients and portions of 95 ml each were placed in tubs:

Thickened skimmed milk, fructose syrup, pieces of strawberry and strawberry puree (15%), plant fat, diet chocolate chips (3.5%, with emulsifier soya lecithin), whey product, red beetroot juice, carob seed flour, guar seed flour, carrageenan, emulsifier (E 471), gelatine, acidifying agent citric acid, strawberry flavouring (containing 1 wt. % phloretin (compound 4), with respect to the total weight of the strawberry flavouring), colorant carotene.

Nutritional value (per 95 ml):
protein 1.8 g, carbohydrate 13.3 g (of which fructose 9.5 g), fat 4.2 g.

Application Example 19

Diet Chocolate Based on Maltite

A chocolate suitable for diabetics was produced from the following ingredients and cast in rectangular slabs:

Maltite, hazel nut composition, cocoa butter, skimmed milk powder, cocoa composition, inulin, pure butter fat, emulsifier soya lecithins, vanilla flavouring (containing vanilla pod extract, vanillin and 1 wt. % phloretin (compound 4), with respect to the total weight of vanilla flavouring).

Nutritional value (per 100 g):
protein 8 g, carbohydrate 43 g (of which maltite 34 g), fat 34 g.

Application Example 20

Diet Chocolate Based on Fructose

A chocolate suitable for diabetics was produced from the following ingredients and cast in rectangular slabs:

Cocoa composition, fructose, skimmed milk powder, cocoa butter, inulin, pure butter fat, emulsifier soya lecithin, walnuts, table salt, vanilla flavouring (containing vanillin and 1 wt. % phloretin (compound 4), with respect to the total weight of vanilla flavouring).

Nutritional value (per 100 g):

protein 8.8 g, carbohydrate 34 g (of which fructose 23 g, lactose 7.5 g, saccharose 1.4 g), fat 36 g; bulk material 18.5 g (of which 12.2 g inulin); sodium: 0.10 g. cocoa content at least 50 wt. %.

Application Example 21

Sugar-Reduced Muesli Mixture

| No. | | A (wt. %) | B (wt. %) |
|---|---|---|---|
| 1 | Oat flakes | 17.00 | 18.90 |
| 2 | Crispy oat flake clusters | 10.00 | 12.00 |
| 3 | Rice Krispies | 16.90 | 17.80 |
| 4 | Cornflakes | 16.50 | 17.50 |
| 5 | Currants | 3.50 | 3.50 |
| 6 | Hazel nuts, chopped | 2.50 | 2.50 |
| 7 | Glucose syrup from wheat, DE 30 | 9.50 | 9.50 |
| 8 | Saccharose | 20.00 | 14.00 |
| 9 | Water | 4.00 | 4.00 |
| 10 | Powdered citric acid, anhydrous | 0.10 | 0.10 |
| 11 | Phloretin (compound 4) 2.5% in 1,2-propylene glycol | — | 0.20 |

The constituents numbered 1 to 6 in each case are mixed in a rotating drum (mix 1). The constituents numbered 7 to 9 in each case are heated and constituent no. 10 is added (and in recipe B constituent no. 11 is also added) (mix 2). Each mix 2 is added to mix 1 and thoroughly mixed. Lastly, the resulting muesli mixture is placed on a baking sheet and dried for 8 minutes in an oven at 130° C.

The perception of sweetness of the full-sugar variant, or recipe A, was classified as virtually identical to that of the muesli mixture with the sugar reduced by 30%, or recipe B, by a group of experts. In an additional triangular test that was also performed, there was found to be no difference in the perception of sweetness.

Application Example 22

Sugar-Reduced Fruit Gums

The perception of sweetness of the full-sugar fruit gum obtained with recipe A given below, was classified as virtually identical to that of the sugar-reduced fruit gum obtained with recipe B (the proportion of saccharose had been reduced by 76%), by a group of experts in both cases. In an additional triangular test that was also performed, there was found to be no difference in the perception of sweetness.

| | A (wt. %) | B (wt. %) |
|---|---|---|
| Water | 23.70 | 25.60 |
| Saccharose | 34.50 | 8.20 |
| Glucose syrup, DE 40 | 31.89 | 30.09 |
| Iso Syrup C* Tru Sweet 01750 (Cerestar GmbH) | 1.50 | 2.10 |
| Gelatine 240 Bloom | 8.20 | 9.40 |
| Polydextrose (Litesse ® Ultra, Danisco Cultor GmbH) | — | 24.40 |
| Yellow and red colorant | 0.01 | 0.01 |
| Citric acid | 0.20 | — |
| Flavouring as in application example 6, preparation F | — | 0.20 |

Polydextrose is a polysaccharide that does not itself taste sweet and that has a low calorific value.

Application Example 23

Chocolate/Cappuccino Ice-Cream

The perception of sweetness of the full-sugar ice-cream obtained with recipe A given below, was classified as identical to that of the sugar-reduced ice-cream obtained with recipe B (the proportion of saccharose had been reduced by 25%), by a group of experts in both cases. In an additional triangular test that was also performed, there was found to be no difference in the perception of sweetness.

| | A (wt. %) | B (wt. %) |
|---|---|---|
| Glucose/fructose syrup | 14.10 | 14.10 |
| Saccharose | 10.00 | 7.50 |
| Skimmed milk powder | 5.00 | 5.00 |
| Cream (36% fat content) | 24.00 | 24.00 |
| Emulsifier and stabiliser Cremodan ® 709VEG (Danisco) | 0.50 | 0.50 |
| Cocoa powder | 5.975 | 5.975 |
| Carrageenan | 0.025 | 0.025 |
| Water | 40.20 | 42.50 |
| Cappuccino flavouring | 0.20 | 0.20 |
| Phloretin (compound 4) 2.5% in 1,2-propylene glycol/ethanol | — | 0.20 |

Application Example 24

Gelatine Capsules for Direct Consumption

| | I (wt. %) | II (wt. %) | III (wt. %) |
|---|---|---|---|
| Gelatine shell: | | | |
| Glycerine | 2.014 | 2.014 | 2.014 |
| Gelatine 240 Bloom | 7.91 | 7.91 | 7.91 |
| Sucralose | 0.065 | 0.065 | 0.065 |
| Allura red | 0.006 | 0.006 | 0.006 |
| Brilliant blue | 0.005 | 0.005 | 0.005 |
| Core composition: | | | |
| Plant oil triglyceride (Coconut oil, fraction) | 79.49 | 68.55 | 58.55 |
| Orange flavouring, containing 1 wt. % phloretin (compound 4), with respect to the total weight of flavouring | 10.0 | 20.0 | 28.65 |
| Neotam and aspartame | 0.01 | 0.05 | — |

-continued

| | I (wt. %) | II (wt. %) | III (wt. %) |
|---|---|---|---|
| Sucralose | 0.10 | 0.15 | 0.40 |
| 2-hydroxypropylmenthyl carbonate | 0.33 | 0.20 | — |
| 2-hydroxyethylmenthyl carbonate | — | 0.20 | 1.00 |
| (1R,3R,4S) menthyl-3-carboxylic-N-ethylamid (WS-3) | — | 0.55 | 0.50 |
| (−)-menthone glycerinacetal (Frescolat MGA) | — | 0.30 | 0.80 |
| Vanillin | 0.07 | — | 0.10 |

The gelatine capsules suitable for direct consumption were produced in accordance with WO 2004/050069 and had a diameter of 5 mm; the ratio by weight of core material to shell material was 90:10. The capsules opened up in the mouth within less than 10 seconds and dissolved completely within less than 50 seconds.

Specific Embodiments

Specific embodiment one comprises use
of a 4-hydroxydihydrochalcone of the formula (I)

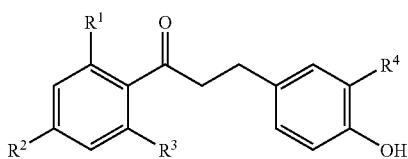

wherein $R^1$, $R^2$, $R^3$ and $R^4$ each, independently, represent H, OH or O-alkyl, with the proviso that at least one of the groups $R^1$, $R^2$ or $R^3$ represents OH, a salt of such a 4-hydroxydihydrochalcone of the formula (I), a mixture containing or consisting of two or more different 4-hydroxydihydrochalcones of the formula (I), wherein $R^1$, $R^2$, $R^3$ and $R^4$ are each defined in the way given above, a mixture containing or consisting of salts of two or more different 4-hydroxydihydrochalcones of the formula (I), wherein $R^1$, $R^2$, $R^3$ and $R^4$ are each defined in the way given above or a mixture containing or consisting of a 4-hydroxydihydrochalcone of the formula (I) or two or more different 4-hydroxydihydrochalcones of the formula (I), wherein $R^1$, $R^2$, $R^3$ and $R^4$ are each defined in the way given above, and a salt of a 4-hydroxydihydrochalcone of the formula (I) or two or more salts of different 4-hydroxydihydrochalcones of the formula (I), wherein $R^1$, $R^2$, $R^3$ and $R^4$ are each defined in the way given above, to enhance the sweet taste of a sweet-tasting substance or the impression of a sweet smell of a flavouring that gives an impression of a sweet smell.

Specific embodiment two comprises a use according to specific embodiment one,
wherein, in formula (I)
$R^1$ represents OH
$R^2$ and $R^3$, independently, represent H or OH,
and
$R^4$ represents H or methoxy.

3. Specific embodiment three comprises a use according to specific embodiment one or two of
a 4-hydroxydihydrochalcone of the formula (I) chosen from the group comprising consisting of
3-(4-hydroxyphenyl)-1-(2-hydroxyphenyl)propan-1-one,
3-(4-hydroxyphenyl)-1-(2,4-dihydroxyphenyl)propan-1-one,
3-(4-hydroxyphenyl)-1-(2,6-dihydroxyphenyl)propan-1-one,
3-(4-hydroxyphenyl)-1-(2,4,6-trihydroxyphenyl)propan-1-one,
3-(4-hydroxy-3-methoxyphenyl)-1-(2-hydroxyphenyl)propan-1-one,
3-(4-hydroxy-3-methoxyphenyl)-1-(2,4-dihydroxyphenyl)propan-1-one,
3-(4-hydroxy-3-methoxyphenyl)-1-(2,6-dihydroxyphenyl)propan-1-one,
3-(4-hydroxy-3-methoxyphenyl)-1-(2,4,6-trihydroxyphenyl)propan-1-one and
3-(3,4-dihydroxyphenyl)-1-(2,4,6-trihydroxyphenyl)propan-1-one,
a salt of such a 4-hydroxydihydrochalcone of the formula (I),
a mixture containing or consisting of two or more 4-hydroxydihydrochalcones of the formula (I) chosen from said group,
a mixture containing or consisting of salts of two or more 4-hydroxydihydrochalcones of the formula (I) chosen from said group
or
a mixture containing or consisting of
a 4-hydroxydihydrochalcone of the formula (I) chosen from said group or two or more 4-hydroxydihydrochalcones of the formula (I) chosen from said group and a salt of a 4-hydroxydihydrochalcone of the formula (I) chosen from said group or two or more salts of different 4-hydroxydihydrochalcones of the formula (I) chosen from said group.

Specific embodiment four comprises a use according to one of the preceding specific embodiments to enhance the sweet taste of a sweet-tasting substance or the impression of a sweet smell of a flavouring that gives the impression of a sweet smell in a preparation used for nutrition, oral hygiene or pleasure.

Specific embodiment five comprises a preparation from the group consisting of preparations, semi-finished products or odour-providing, flavour-providing or taste-providing compositions or mixtures of spices used for nutrition, oral hygiene or pleasure, containing the following components:
(a)
a 4-hydroxydihydrochalcone of the formula (I)

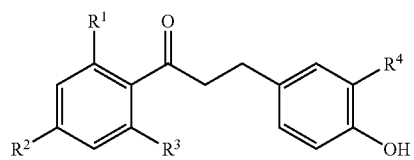

wherein
$R^1$, $R^2$, $R^3$ and $R^4$ each, independently, represent H, OH or O-alkyl, with the proviso that at least one of the groups $R^1$, $R^2$ or $R^3$ represents OH, a salt of such a 4-hydroxydihydrochalcone of the formula (I), a mixture containing or consisting of two or more different 4-hydroxydihydrochalcones of the formula (I), wherein $R^1$, $R^2$, $R^3$ and $R^4$ are each defined in the way given above, a mixture containing or consisting of salts of two or more different 4-hydroxydihydrochalcones of the formula (I), wherein $R^1$, $R^2$, $R^3$ and $R^4$ are each defined in the way given above or a mixture containing or consisting of a 4-hydroxydihydrochalcone of the formula (I) or two or more different 4-hydroxydihydrochalcones of the formula (I), wherein $R^1$, $R^2$, $R^3$ and $R^4$ are each defined in the way given above, and a salt of a 4-hydroxydihydrochalcone of the formula (I) or two or more salts of different 4-hydroxydihydrochalcones of the formula (I), wherein $R^1$, $R^2$, $R^3$ and $R^4$ are each defined in the way given above, as well as (b) one or more other sweet-tasting substances and/or (c) one or more flavourings that give the impression of a sweet smell, wherein the total amount of component (a) in the preparation is sufficient to enhance to an overproportional extent the impression of a sweet taste of the sweet-tasting substance(s) (b) or the impression of a sweet smell flavouring(s) (c) that give an impression of a sweet smell.

Specific embodiment six comprises a preparation according to specific embodiment five, wherein in formula (I)

$R^1$ represents OH $R^2$ and $R^3$, independently, represent H or OH, and $R^4$ represents H or methoxy ($OCH_3$).

Specific embodiment seven comprises a preparation according to specific embodiment five or six, containing as component (a):

a 4-Hydroxydihydrochalcone of the formula (I) chosen from the group consisting of comprising 3-(4-hydroxyphenyl)-1-(2-hydroxyphenyl)propan-1-one,
3-(4-hydroxyphenyl)-1-(2,4-dihydroxyphenyl)propan-1-one,
3-(4-hydroxyphenyl)-1-(2,6-dihydroxyphenyl)propan-1-one,
3-(4-hydroxyphenyl)-1-(2,4,6-trihydroxyphenyl)propan-1-one,
3-(4-hydroxy-3-methoxyphenyl)-1-(2-hydroxyphenyl)propan-1-one,
3-(4-hydroxy-3-methoxyphenyl)-1-(2,4-dihydroxyphenyl)propan-1-one,
3-(4-hydroxy-3-methoxyphenyl)-1-(2,6-dihydroxyphenyl)propan-1-one,
3-(4-hydroxy-3-methoxyphenyl)-1-(2,4,6-trihydroxyphenyl)propan-1-one and
3-(3,4-dihydroxyphenyl)-1-(2,4,6-trihydroxyphenyl)propan-1-one, a salt of such a 4-Hydroxydihydrochalcone of the formula (I), a mixture containing or consisting of two or more 4-hydroxydihydrochalcones of the formula (I) chosen from said group, a mixture containing or consisting of salts of two or more 4-hydroxydihydrochalcones of the formula (I) chosen from said group or a mixture containing or consisting of one of the 4-hydroxydihydrochalcones of the formula (I) chosen from said group or two or more 4-hydroxydihydrochalcones of the formula (I) chosen from said group and a salt of a 4-hydroxydihydrochalcones of the formula (I) chosen from said group or two or more salts of different 4-hydroxydihydrochalcones of the formula (I) chosen from said group.

Specific embodiment eight comprises a preparation according to one of specific embodiment five to seven, containing as component (b) one or more sugars, wherein the total amount of (i) 4-hydroxy-dihydrochalcones of the formula (I) and (ii) their salts (component (a)) in the preparation is sufficient to convey the same or an enhanced impression of sweetness as a preparation or semi-finished product that otherwise has an identical composition that contains neither (i) 4-hydroxydihydrochalcones of the formula (I) nor (ii) their salts, but at least 1.05 times the amount of sugar.

Specific embodiment nine comprises a preparation according to one of specific embodiments 5 to 8, wherein the ratio of the total amount of (i) 4-hydroxydihydrochalcones of the formula (I) and (ii) their salts contained therein to the total amount of glycosides of the (i) 4-hydroxydihydrochalcones of the formula (I) and (ii) their salts used is greater than 1:3, preferably greater than 1:1, particularly preferably greater than 10:1.

Specific embodiment ten comprises a preparation according to one of specific embodiments 5 to 9, wherein the preparation contains phloretin and also either (a) contains no phloridzin or (b) contains phloridzin, wherein the ratio of the amount of phloretin to the amount of phloridzin is greater than 1:3, preferably greater than 1:1, particularly preferably greater than 10:1.

Specific embodiment eleven comprises a preparation according to one of specific embodiments five to ten, containing (b) one or more further sweet-tasting substances, wherein the further sweet-tasting substance(s) is/are chosen from the group consisting of comprising:

(i) one or more carbohydrates chosen from the group consisting of comprising sucrose, trehalose, lactose, maltose, melizitose, melibiose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, maltodextrin and plant preparations containing one or more of the carbohydrates mentioned, (ii) one or more sugar alcohols chosen from the group consisting of comprising glycerine, erythritol, threitol, arabitol, ribitol, xylitol, sorbitol, mannitol, maltitol, isomaltitol, dulcitol and lactitol, (iii) one or more proteins and/or amino acids from the group consisting of comprising miraculin, monellin, thaumatin, curculin, brazzein, glycine, D-leucine, D-threonine, D-asparagine, D-phenylalanine, D-tryptophanetryptophan, L-proline, (iv) one or more sweet substances from the group consisting of comprising magap, sodium cyclamate, acesulfame K, neohesperidindihydrochalcone, sodium salt of saccharin, aspartame, superaspartame, neotam, alitam, sucralose, stevioside, rebaudioside, lugduname, carrelame, sucrononates, sucrooctates, monatin and phyllodulcin, and mixtures of these and/or (c) one or more flavourings that give an impression of a sweet smell, wherein the further flavourings that give an impression of a sweet smell are chosen from the group consisting of comprising:

vanillin, ethylvanillin, ethylvanillin isobutyrate (=3-ethoxy-4-isobutyryloxybenzaldehyde), Furaneol® (2,5-dimethyl-4-hydroxy-3(2H)-furanone) and derivatives thereof (e.g. homofuraneol, 2-ethyl-4-hydroxy-5-methyl-3(2H)-furanone), homofuronol (2-ethyl-5-methyl-4-hydroxy-3(2H)-furanone and 5-ethyl-2-methyl-4-hydroxy-3(2H)-furanone), maltol and derivatives thereof (e.g. ethylmaltol), coumarin and derivatives thereof, gamma-lactones (e.g. gamma-undecalactone, gamma-nonalactone), delta-lactones (e.g. 4-methyl-delta-lactone, massoilactone, delta-decalactone, tuberolactone), methyl sorbate, divanillin, 4-hydroxy-2(or 5)-ethyl-5(or 2)-methyl-3(2H)furanone, 2-hydroxy-3-methyl-2-cyclopentenones, 3-hydroxy-4,5-dimethyl-2(5H)-furanone, fruit esters and fruit lactones (e.g. n-butyl acetate, isoamyl acetate, ethyl propionate, ethyl butyrate, n-butyl butyrate, isoamyl butyrate, ethyl 3-methyl-butyrate, ethyl n-hexanoate, allyl n-hexanoate, n-butyl n-hexanoate, ethyl n-octanoate, ethyl-3-methyl-3-phenylglycidate, ethyl-2-trans-4-cis-decadienoate), 4-(p-hydroxyphenyl)-2-butanone, 1,1-dimethoxy-2,2,5-trimethyl-4-hexane, 2,6-dimethyl-5-hepten-1-al and phenylacetaldehyde.

Specific embodiment twelve comprises the preparation used for nutrition, oral hygiene or pleasure according to one of specific embodiments five to eleven, containing a total amount of less than 0.025 wt. % (250 ppm), preferably less than 0.02 wt. % (200 ppm), of (i) 4-hydroxydihydrochalcones of the formula (I) and (ii) their salts, with respect to the total weight of the preparation.

Specific embodiment thirteen comprises the preparation used for nutrition, oral hygiene or pleasure according to one of specific embodiments five to twelve, containing a total amount in the range 0.1 to 150 ppm, preferably in the range 1 to 50 ppm, particularly preferably in the range 10 to 50 ppm, of (i) 4-hydroxydihydrochalcones of the formula (I) and (ii) their salts, with respect to the total weight of the preparation.

Specific embodiment fourteen comprises a preparation used for nutrition, oral hygiene or pleasure according to one of specific embodiments five to thirteen, wherein the preparation is chosen from the group consisting of:
(A) confectionery,
(B) alcoholic or non-alcoholic drinks or instant drinks,
(C) cereal products and/or nut products,
(D) milk products,
(E) fruit and/or vegetable preparations,
(F) Products based on fat or oil or emulsions of the same
(G) oral hygiene products.

Specific embodiment fifteen comprises a preparation used for nutrition, oral hygiene or pleasure according to one of specific embodiments five to fourteen, containing
component (a), containing or consisting of phloretin,
component (b), containing or consisting of one or more sugars,
and also optionally
component (c),
wherein the total amount of component (a) in the preparation
is sufficient to convey the same or an enhanced impression of sweetness as a preparation with an otherwise identical composition that contains neither (i) 4-hydroxydihydrochalcones of the formula (I) nor (ii) their salts, but contains at least 1.05 times the amount of sugar
and/or
is present within the range 0.1 to 150 ppm,
and wherein the preparation either
(A) contains no phloridzin
or
(B) contains phloridzin, wherein the ratio of the amount of phloretin to the amount of phloridzin is greater than 1:3, preferably greater than 1:1, particularly preferably greater than 10:1.

Specific embodiment sixteen comprising a preparation according to one of specific embodiments five to eleven, chosen from the group consisting of semi-finished products, odour-providing, flavour-providing or taste-providing compositions or mixtures of spices, containing a total amount in the range 0.0001 wt. % to 95 wt. %, preferably 0.001 wt. % to 80 wt. %, particularly preferably 0.001 wt. % to 50 wt. %, of (i) 4-hydroxydihydrochalcones of the formula (I) or (ii) their salts, with respect to the total weight of the preparation.

Specific embodiment seventeen comprises semi-finished products according to one of specific embodiments five to eleven or sixteen, characterised in that it is spray-dried.

Specific embodiment eighteen comprises a preparation according to one of specific embodiments five to seventeen, containing
as additional component (d)
one or more esters chosen from the group consisting of comprising $C_1$-$C_6$-esters of lactic acid, di-$C_1$-$C_4$-esters of tartaric acid, di-$C_1$-$C_4$-esters of succinic acid, di-$C_1$-$C_4$-esters of malonic acid, di-$C_1$-$C_4$-esters of malic acid, di-$C_1$-$C_4$-esters of citric acid and tri-$C_1$-$C_4$-esters of citric acid,
and/or
one or more solvents chosen from the group consisting of comprising 1,2-propylene glycol, dimethylsulfoxide, ethanol, and ethanol/water mixtures.

Specific embodiment nineteen comprises a preparation according to one of specific embodiments five to eighteen, also containing at least one other substance for masking or minimising a bitter, metallic, limey, acidic or astringent impression of taste or to enhance an impression of a sweet, salty or umami taste.

Specific embodiment twenty comprises a preparation according to one of specific embodiment five to nineteen, also containing hesperetin or its salts.

Specific embodiment twenty one comprises a process for enhancing the sweet taste of a sweet-tasting substance or the impression of a sweet smell of a flavouring that gives an impression of a sweet smell using the following step:
mixing one or more sweet-tasting substances (component (b)) or one or more flavourings that give an impression of a sweet smell (component (c)) with a total amount of component (a) as defined in one of specific embodiments five to seven,
wherein the total amount of component (a) in the preparation is sufficient to enhance the impression of a sweet taste of the sweet-tasting substance(s) (b) or the impression of a sweet smell of the flavouring(s) (c) that give an impression of a sweet smell.

Specific embodiment twenty-two comprises a process according to specific embodiment twenty-one, wherein the ratio of the amount of (i) 4-hydroxydihydrochalcones of the formula (I) and (ii) their salts present in component (a) to the total amount of optionally used glycosides of the (i) 4-hydroxydihydrochalcones of the formula (I) and (ii) their salts used in component (a) is at least greater than 1:3, preferably greater than 1:1, particularly preferably greater than 10:1.

Specific embodiment twenty-three comprises a process according to specific embodiment twenty-one or twenty-two, wherein component (a) contains phloretin and either
(A) contains no phloridzin
or
(B) contains phloridzin, wherein the ratio of the amount of phloretin to the amount of phloridzin is greater than 1:3, preferably greater than 1:1, particularly preferably greater than 10:1.

Specific embodiment twenty-four comprises 3-(4-hydroxy-3-methoxyphenyl)-1-(2,4,6-trihydroxyphenyl)propan-1-one (2',4,4',6'-tetrahydroxy-3-methoxydihydrochalcone; compound 8).

The invention claimed is:

1. An oral hygiene or consumable preparation comprising:
   (a) 0.1 to 150 ppm of phloretin (3-(4-hydroxyphenyl)-1-(2,4,6-trihydroxyphenyl)propan-1-one); and
   (b) one or more sweet-tasting substance selected from the group consisting of sucrose, glucose, fructose, maltitol, erythritol, sorbitol, mannitol, neohesperidin dihydrochalcone, thaumatin, stevioside, rebaudioside, and palatinose;
   wherein the (a) phloretin, and the (b) one or more sweet-tasting substances in the preparation are in amounts such that the sweet taste of the sweet-tasting substance is synergistically enhanced by at least 1.2 times, in comparison to an otherwise identical preparation without the (a) phloretin;
   wherein the preparation is suitable for introduction into a person's mouth; and
   wherein the preparation:
   (a) contains no phloridzin, or
   (b) contains phloridzin, but the ratio of the amount of phloretin to the amount of phloridzin is greater than 1:1.

2. The preparation according to claim 1, further comprising:
   (c) one or more flavourings that give an impression of a sweet smell, wherein the further flavorings that give an impression of a sweet smell are selected from the group consisting of: vanillin, ethylvanillin, ethylvanillin isobutyrate, 2,5-dimethyl-4-hydroxy-3(2H)-furanone, 2-ethyl-4-hydroxy-5-methyl-3(2H)-furanone, 2-ethyl-5-methyl-4-hydroxy-3(2H)-furanone 5-ethyl-2-methyl-4-hydroxy-3(2H)-furanone], maltol, ethylmaltol, coumarin, gamma-lactones, delta-lactones, methyl sorbate, divanillin, 4-hydroxy-2(or 5)-ethyl-5 (or 2)-methyl-3 (2H)furanone, 2-hydroxy-3-methyl-2-cyclopentenones, 3-hydroxy-4, 5-dimethyl-2(5H)-furanone, fruit esters and fruit lactones, 4-(p-hydroxyphenyl)-2-butanone, 1,1-dimethoxy-2,2, 5-trimethyl-4-hexane, 2,6-dimethyl-5-hepten-1-al and phenylacetaldehyde.

3. The preparation according to claim 1, wherein the preparation is selected from the group consisting of:
   (A) a confectionery,
   (B) an alcoholic or non-alcoholic drink and/or instant drink,
   (C) a cereal product and/or a nut product,
   (D) a milk product,
   (E) a fruit and/or vegetable preparation,
   (F) a product based on fat or oil or an emulsions of the same, and
   (G) an oral hygiene product.

4. The preparation according to claim 1 selected from the group consisting of, an odor-providing, flavor-providing or taste-providing composition, and a mixtures of spices.

5. The preparation according to claim 4 that is a spray-dried product.

6. The preparation according to claim 1, further comprising:
   (d) one or more esters chosen from the group consisting of $C_1$-$C_6$-esters of lactic acid, di-$C_1$-$C_4$-esters of tartaric acid, di-$C_1$-$C_4$-esters of succinic acid, di-$C_1$-$C_4$-esters of malonic acid, di-$C_1$-$C_4$-esters of malic acid, di-$C_1$-$C_4$-esters of citric acid and tri-$C_1$-$C_4$-esters of citric acid, and/or one or more solvents chosen from the group consisting of 1,2-propylene glycol, dimethylsulfoxide, ethanol, and ethanol/water mixtures.

7. The preparation according to claim 1, further comprising:
   (e) one or more substances for masking or minimising a bitter, metallic, limey, acidic or astringent impression of taste or to enhance an impression of a sweet, salty or umami taste.

8. The preparation according to claim 1 comprising hesperetin or a salt thereof.

9. A method for enhancing the sweetness of an oral hygiene or consumable preparation comprising adding to the preparation:
   (a) 0.1 to 150 ppm of phloretin (3-(4-hydroxyphenyl)-1-(2,4,6-trihydroxyphenyl)propan-1-one);
   (b) one or more sweet-tasting substance selected from the group consisting of sucrose, glucose, fructose, maltitol, erythritol, sorbitol, mannitol, neohesperidin dihydrochalcone, thaumatin, stevioside, rebaudioside, and palatinose;
   wherein the (a) phloretin, and the (b) one or more sweet-tasting substances in the preparation are in amounts such that the sweet taste of the sweet-tasting substance is enhanced by at least 1.2 times, in comparison to an otherwise identical preparation without the (a) phloretin;
   wherein the preparation is suitable for introduction into a person's mouth; and
   wherein the preparation:
   (a) contains no phloridzin, or
   (b) contains phloridzin, but the ratio of the amount of phloretin to the amount of phloridzin is greater than 1:1.

10. The method according to claim 9, wherein the preparation further comprises:
    (c) one or more flavourings that give an impression of a sweet smell, wherein the further flavorings that give an impression of a sweet smell are selected from the group consisting of: vanillin, ethylvanillin, ethylvanillin isobutyrate, 2,5-dimethyl-4-hydroxy-3(2H)-furanone, 2-ethyl-4-hydroxy-5-methyl-3(2H)-furanone, 2-ethyl-5-methyl-4-hydroxy-3(2H)-furanone 5-ethyl-2-methyl-4-hydroxy-3(2H)-furanone], maltol, ethylmaltol, coumarin, gamma-lactones, delta-lactones, methyl sorbate, divanillin, 4-hydroxy-2(or 5)-ethyl-5 (or 2)-methyl-3(2H)furanone, 2-hydroxy-3-methyl-2-cyclopentenones, 3-hydroxy-4,5-dimethyl-2(5H)-furanone, fruit esters and fruit lactones, 4-(p-hydroxyphenyl)-2-butanone, 1,1-dimethoxy-2,2,5-trimethyl-4-hexane, 2,6-dimethyl-5-hepten-1-al and phenylacetaldehyde.

11. The method according to claim 9, wherein the preparation is selected from the group consisting of:
    (A) a confectionery,
    (B) an alcoholic or non-alcoholic drink and/or instant drink,
    (C) a cereal product and/or a nut product,
    (D) a milk product,
    (E) a fruit and/or vegetable preparation,
    (F) a product based on fat or oil or an emulsions of the same, and
    (G) an oral hygiene product.

12. A method according to claim 9, wherein the preparation is selected from the group consisting of a semi-finished product, an odor-providing, flavor-providing or taste-providing composition, and a mixtures of spices.

13. The method according to claim 12, wherein the preparation is a semi-finished product that is spray-dried.

14. The method according to claim 9, wherein the preparation further comprises:
   (d) one or more esters chosen from the group consisting of $C_1$-$C_6$-esters of lactic acid, di-$C_1$-$C_4$-esters of tartaric acid, di-$C_1$-$C_4$-esters of succinic acid, di-$C_1$-$C_4$-esters of malonic acid, di-$C_1$-$C_4$-esters of malic acid, di-$C_1$-$C_4$-esters of citric acid and tri-$C_1$-$C_4$-esters of citric acid, and/or one or more solvents chosen from the group consisting of 1,2-propylene glycol, dimethylsulfoxide, ethanol, and ethanol/water mixtures.

15. The method according to claim 9, wherein the preparation further comprises:
   (e) one or more substances for masking or minimising a bitter, metallic, limey, acidic or astringent impression of taste or to enhance an impression of a sweet, salty or umami taste.

16. The method according to claim 9, wherein the preparation comprises hesperetin or a salt thereof.

17. The preparation according to claim 1, wherein the preparation does not include sugar alcohols.

18. The preparation according to claim 1, wherein the one or more sweet-tasting substance is selected from the group consisting of sucrose, glucose, fructose, maltitol, erythritol, sorbitol, mannitol, and palatinose.

19. The preparation according to claim 1, wherein the sweet-tasting substance is sucrose.

* * * * *